US008906425B2

(12) United States Patent
Perrier et al.

(10) Patent No.: US 8,906,425 B2
(45) Date of Patent: Dec. 9, 2014

(54) STIMULATION OF THE SYNTHESIS OF THE ACTIVITY OF AN ISOFORM OF LYSYL OXIDASE-LIKE LOXL FOR STIMULATING THE FORMATION OF ELASTIC FIBERS

(75) Inventors: Eric Perrier, Les Cotes D'arey (FR); Valérie Cenizo, Vaulx-Millieu (FR); Charbel Bouez, Lyons (FR); Pascal Sommer, Saint Genis Laval (FR); Odile Damour, Saint Genis Laval (FR); Claudine Gleyzal, Lyons (FR); Valérie Andre, Ampuis (FR); Corinne Reymermier, Charly (FR)

(73) Assignees: BASF Beauty Care Solutions France S.A.S., Lyon (FR); Centre National de la Recherche Scientifique, Paris (FR)

( * ) Notice: Subject to any disclaimer, the term of this patent is extended or adjusted under 35 U.S.C. 154(b) by 41 days.

(21) Appl. No.: 13/618,038

(22) Filed: Sep. 14, 2012

(65) Prior Publication Data

US 2013/0011902 A1 Jan. 10, 2013

Related U.S. Application Data

(60) Division of application No. 12/824,855, filed on Jun. 28, 2010, which is a continuation of application No. 10/852,065, filed on May 24, 2004, now abandoned.

(30) Foreign Application Priority Data

Jun. 13, 2003 (FR) ...................................... 03 07177

(51) Int. Cl.
| | | |
|---|---|---|
| *A61K 8/97* | (2006.01) | |
| *A61K 36/28* | (2006.01) | |
| *A61K 8/66* | (2006.01) | |
| *A61Q 19/08* | (2006.01) | |
| *A61K 36/185* | (2006.01) | |
| *A61K 35/74* | (2006.01) | |
| *A61K 36/31* | (2006.01) | |
| *A61K 36/896* | (2006.01) | |
| *C12N 9/06* | (2006.01) | |
| *A61K 36/9064* | (2006.01) | |
| *A61K 36/23* | (2006.01) | |
| *A61K 36/81* | (2006.01) | |
| *A61K 36/54* | (2006.01) | |
| *A61K 36/899* | (2006.01) | |
| *A61Q 19/00* | (2006.01) | |
| *A61K 38/00* | (2006.01) | |

(52) U.S. Cl.
CPC . *A61K 35/74* (2013.01); *A61K 8/66* (2013.01); *A61K 38/00* (2013.01); *A61Q 19/08* (2013.01); *A61K 36/185* (2013.01); *A61K 36/31* (2013.01); *A61K 36/896* (2013.01); *C12N 9/0022* (2013.01); *A61K 36/9064* (2013.01); *A61K 36/23* (2013.01); *A61K 36/81* (2013.01); *G01N 2500/04* (2013.01); *A61K 36/54* (2013.01); *A61K 36/899* (2013.01); *C12Y 104/03013* (2013.01); *A61Q 19/00* (2013.01)
USPC ........... 424/725; 424/764; 424/756; 424/630; 424/55; 514/18.8

(58) Field of Classification Search
USPC ............... 424/725, 764, 756, 630, 7, 55, 757; 514/18.8
See application file for complete search history.

(56) References Cited

U.S. PATENT DOCUMENTS

| | | | |
|---|---|---|---|
| 4,238,509 A | 12/1980 | Evans et al. | |
| 4,942,033 A | 7/1990 | Aubert et al. | |
| 4,997,649 A | 3/1991 | Papaconstantin et al. | |
| 6,140,056 A | 10/2000 | Khodadoust | |
| 6,270,811 B1 | 8/2001 | Fregonese | |
| 6,277,622 B1 | 8/2001 | Weiss | |
| 6,300,092 B1 | 10/2001 | Khodadoust et al. | |
| 6,391,602 B1 | 5/2002 | Khodadoust | |
| 2002/0150564 A1 | 10/2002 | Ensley | |

FOREIGN PATENT DOCUMENTS

| | | |
|---|---|---|
| CA | 2 327 003 A1 | 5/2002 |
| DE | 1 468 295 A1 | 5/1969 |
| EP | 0 296 078 A1 | 12/1988 |
| EP | 0 374 440 A2 | 6/1990 |
| EP | 0 953 340 A1 | 11/1999 |
| FR | 2 718 752 A1 | 10/1995 |
| FR | 2 828 206 A1 | 2/2003 |
| JP | 60156618 A | 8/1985 |
| JP | 11158078 A | 6/1999 |
| JP | 2001220313 A | 8/2001 |
| JP | 2002272470 A | 9/2002 |
| JP | 2002275079 A | 9/2002 |

(Continued)

OTHER PUBLICATIONS

First outlines: A Dictionary of the Solubilities of Chemical Substances, 1863: On p. 254, first column.*
Daithankar, et al., "(Evaluation of Mositurizing Efficiency of Silk Proteins I: Silk Fibroin.), Which Was Part of the International Pharmaceutical Federation World Congress", vol. 62, (2002), p. 33. See Abstract.
Voegeli, et al., "Cosmetic News", vol. 18, No. 103, (1995), pp. 236-242. See Abstract.
Molnar, et al., "Structural and Dunctional Diversity of Lysyl Oxidase and the LOX-Like Proteins", Biochimica et Biophysica Acta, vol. 1647, No. 1-2, (2003), pp. 220-224.
Saito et al., "Regulation of a Novel Gene Encoding a Lysyl Oxidase-Related Protein in Cellular Adhesion and Senescence", The Journal of Biological Chemistry, vol. 272, No. 14, (1997), pp. 8157-8160.

(Continued)

*Primary Examiner* — Kagnew H Gebreyesus
(74) *Attorney, Agent, or Firm* — Drinker Biddle & Reath LLP

(57) ABSTRACT

The invention relates to the stimulation of the synthesis and of the activity of an isoform of lysyl oxidase, and more particularly of the LOXL (lysyl oxidase-like) isoform. The invention relates notably to a method of identifying an active principle which stimulates the formation of elastic fibers. The aim of the invention is mainly to provide such a method of identification so as to provide compositions which enable stimulating the formation of elastic fibers.

20 Claims, 9 Drawing Sheets

(56) References Cited

FOREIGN PATENT DOCUMENTS

Figure 3:
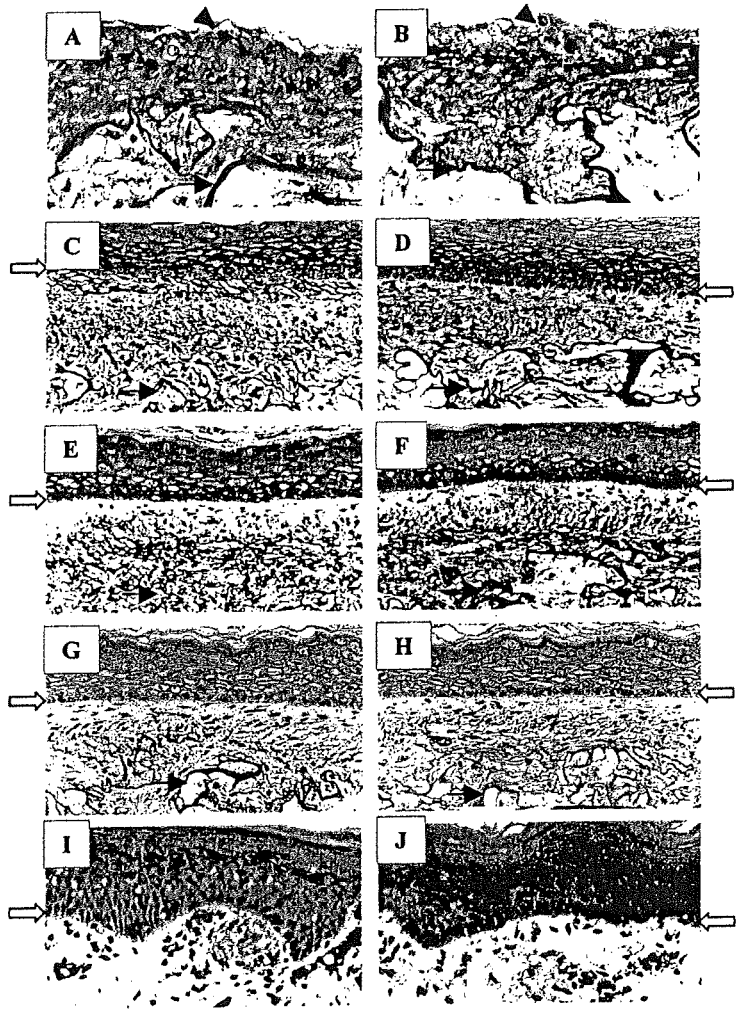

| JP | 2003113392 A | 4/2003 |
|---|---|---|
| JP | 2003155246 A | 5/2003 |
| JP | 2004018431 A | 1/2004 |
| JP | 2004131699 A | 4/2004 |
| WO | WO-97/48823 A1 | 12/1997 |
| WO | WO-98/06830 A1 | 2/1998 |
| WO | WO-99/60989 A2 | 12/1999 |
| WO | WO-00/44910 A1 | 8/2000 |
| WO | WO-01/83702 A2 | 11/2001 |
| WO | WO-01/91821 A1 | 12/2001 |
| WO | WO-01/92322 A1 | 12/2001 |
| WO | WO-02/11667 A2 | 2/2002 |
| WO | WO-02/30438 A1 | 4/2002 |
| WO | WO-02/055049 A1 | 7/2002 |
| WO | WO-02/061092 A2 | 8/2002 |

OTHER PUBLICATIONS

Csiszar, "Lysal Oxidaes: A Novel Multifunctional Amine Oxidase Family", In Progress in Nucleic Acid Research and Molecular Biology, MOLDAVE (Ed.), vol. 70, (2001), pp. 2-28.

Seve et al., "Expression Analysis of Recombinant Lysyl Exidae (LOX in Myofibroblastlike Cells", Connective Tissue Research, vol. 43, (2002), pp. 613-619.

Ashcroft et al., "Age-Related Changes in the Temporal and Spatial Distribution of Fibrillin and Elastin mRNAs and Proteins in Acute Cutaneous Wounds of Healthy Adults", Journal of Pathology, vol. 183, (1997), pp. 80-89.

Watson et al., "FibrillinOrich Microfibrils are Reduces in Photoaged Skin. Distribution at the Dermal-Epidermal Junction", The Journal of Investigative Dermatology, vol. 112, No. 3, (1999), pp. 782-787.

Pasquali-Ronchetti et al., "Elastic Fiber During Development and Aging", Microscopy Research and Technique, vol. 38, (1997), pp. 428-435.

Duplan-Perrat, "Keratinocyles Influence the Maturation and Organization of the Elastin Network in a Skin Equivalent", The Journal of Investigative Dermatology, vol. 114, No. 2, (2000), pp. 365-370.

Michel et al., "Characterization of a New Tissue-Engineered Human Skin Equivalent With Hair", In Vivo Cell Dev. Biol.-Animal, vol. 35, (1999), pp. 318-326.

Decitre et al., "Lysyl Oxidase-Like Protein Localizes to Sites of de novo Fibronogenesis in Fibrosis and in the Early Stromal Reaction of Ductal Breast Carcinomas", Laboratory Investigation, vol. 78, No. 2, (1998), pp. 143-151.

Borel et al., "Lysyl Oxidase-Like Protein From Bovine Aorta", The Journal of Biological Chemistry, vol. 276, No. 52, (2001), pp. 48944-48949.

Kenyon et al., "A Novel Human cDNA with a Predicted Protein Similar to Lysys Oxidase Maps to Chromosome 15q24-q25", The Journal of Biological Chemistry, vol. 268, No, 25, (1993), pp. 18435-18437.

Boak et al., "Regulation of Lysyl Oxidase Expression in Lung Fibroblasts by Transforming Growth Factor-62 , and Prostaglandin $E_2$,", American Journal of Respiratory Cell and Molecular Biology, vol. 11, (1994), pp. 751-755.

Wachi et al., "Endothelin-1 Down-Regulates Expression of Tropoelastin and Lysyl Oxidale mRNA in Cultured Chick Aortic Smooth Muscle Cells", Journal of Health Science, vol. 47, No. 6, (2001), pp. 525-532.

Kagan et al., "Control of Elastin Metabolism by Elastin Ligands", The Journal of Biological Chemistry, vol. 256, No. 11, (1981), pp. 5417-5421.

Smith-Mungo et al., "Lysyloxidase: Properties, Regulation and Multiple Functions in Biology", Matrix Biology, vol. 16, (1997/1998), pp. 387-298.

Jeay et al., "Lysyl Oxidase Inhibits Ras-Mediated Transformation by Preventing Activating of $NF_{-\kappa}B$", Molecular and Cellular Biology, vol. 23, No. 7, (2003), pp. 2251-2263.

Brassert et al., "Conformational Dependence of Collagenase (Matrix Metalloproteinase-1) Up-Regulation of Elastin Peptides in Cultured Fibroblasts", the Journal of Biological Chemistry, vol. 276, No. 7, (2001), pp. 5222-5227.

Co-pending U.S. Appl. No. 10/852,575, entitled, "Stimulation of the Activity of an Isoform of Lysyl Oxidase for Combating Against Some Pathologies Due to an Incomplete, Absent or Disorganized Elastogenesis", filed May 24, 2004.

Noblesse, et al., "Lysyl-Oxidase-Like and Lysyl Oxidase are Present in the Dermis and Epidermis of a Skin Equivalent and in Human Skin and are Associated in Elastic Fibers", Invest. Dermatol., vol. 122, No. 3, (2004), pp. 621-630.

Kagan, "Intro- and Extracellular Enzymes of Collagen Biosynthesis as Biological and Chemical Targets in the Control of Fibrosis", Acta Tropica, vol. 77, (2000), pp. 147-152.

Kielty, et al., "Elastic Fibers", Journal of Cell Science, vol. 115, (2002), pp. 2817-2828.

Kirschmann, et al., "A Molecular Role for Lysyl Oxidase in Breast Cancer Invasion", Cancer Research, vol. 62, (2002), pp. 4478-4483.

Liu, et al., "Elastic Fiber Homeostasis Requires Lysyl Oxidase-Like 1 Protein", Nat. Genet., vol. 36, No. 2, (2004), pp. 78-82.

Summary from EPODOC, Derwent, and JPO for JP 2003-95913 in English.

Computer translation of JP 2000-63227.

The Scientific Committee on Cosmetic Products and Non-Food Products Intended for Consumers (SCCNFP/0389/00 Final), pp. 1-307, 2002.

The Scientific Committee on Cosmetic Products and Non-Food Products Intended for Consumers (SCCNFP), Oct. 2000.

* cited by examiner

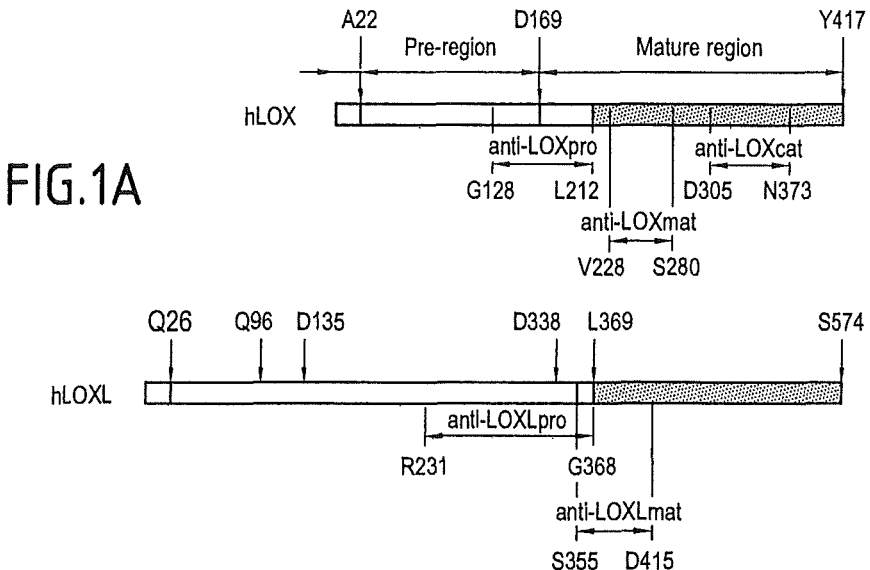
FIG.1A
FIG.1B
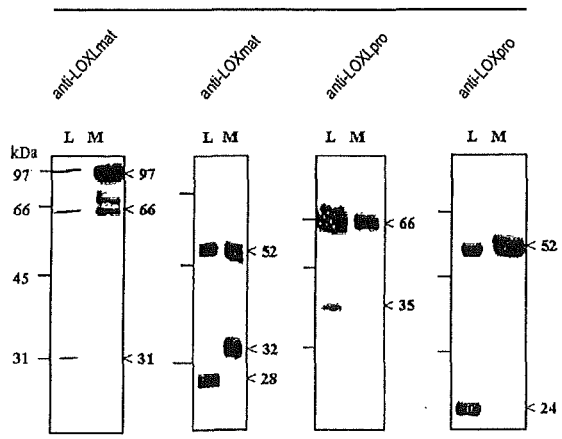
FIG.2

STIMULATION OF THE SYNTHESIS OF THE ACTIVITY OF AN ISOFORM OF LYSYL OXIDASE-LIKE LOXL FOR STIMULATING THE FORMATION OF ELASTIC FIBERS

RELATED APPLICATIONS

This application is a divisional of U.S. Ser. No. 12/824,855, filed Jun. 28, 2010, which is a continuation of U.S. Ser. No. 10/852,065, filed May 24, 2004, which claims benefit of French application 03 07177, filed Jun. 13, 2003. The entire content of each above-mentioned application is hereby incorporated by reference in its entirety.

SUBMISSION OF SEQUENCE LISTING

The Sequence Listing associated with this application is filed in electronic format via EFS-Web and hereby is incorporated by reference into the specification in its entirety. The name of the text file containing the Sequence Listing is Sequence_Listing_17587_00048. The size of the text file is 31 KB; the text file was created on Sep. 14, 2012.

The invention relates to the stimulation of the activity of an isoform of lysyl oxidase, and more particularly of the LOXL (lysyl oxidase-like) isoform.

STATE OF THE ART

The properties of resistance and of elasticity of the skin and of the mucous membranes are essentially defined by the collagen fibers and elastin fibers of the dermis. Elastin is a protein which makes up the elastic fibers by combining itself with other molecules such as fibrillins and MAGPs (Microfibrillar. Associated Glycoproteins).

The elastic fibers are formed of elastin deposited on the microfibrils. Elastin is synthesized in the form of soluble tropoelastin which acquires its physicochemical properties (insolubility, elasticity) after the intra- and inter-molecular cross-linking of it by a lysyl oxidase, and its deposit on the microfibrils. The elastic fibers are responsible for the elastic property of the organs which contain them (vessels, pulmonary parenchyma, elastic cartilages, skin . . . ). The elastic fibers are mainly constituted of elastin deposited on the microfibrils. The name « elastin » was reserved to the protein which forms the amorphous portion of the elastic fibers and which imparted their elasticity to them. Recently, components of these elastic fibers have been shown in the epidermis.

The collagen fibrils are formed by the trimeric assembly of chains of collagen. These collagen fibers are also cross-linked by a lysyl oxidase.

Ageing of skins and of mucous membranes is associated with a modification of these fibrillar networks, notably that of the elastic fibers which degrade and which do not re-form correctly. Similarly, in scars, the network of elastic fibers does not form correctly. Five known isoforms exist in the family of lysyl oxidases (LOs): LOX, LOXL, LOXL2, LOXL3, LOXL4 (Csiszar, Lysyl oxidases: A novel multifunctional amine oxidase family, Nucleic Acid Research and Molecular Biology, 2001, vol 70, p2-28). LOX is, clearly involved in the cross-linking of collagen fibers (Seve et al., Expression analysis of recombinant lysyl oxidase (LOX) in myofibroblast-like cells, Connective Tissue Research, 2002, 43: 613-619).

Functional elastic fibers (which are mainly found in the skin, the vessels, the retina, the macula of the retina and the inter-vertebral discs) are formed during prenatal development and immediately after birth. In the skin, these elastic fibers are formed by the fibroblasts of the dermis, but certain compounds, which are necessary for the elaboration of the elastic fibers, have also been found in the cells of the epidermis. The collagen fibers are synthesized in the connective tissues throughout the whole life.

The rate of replacement of the elastic fibers is very low in adult life, although the overall level of elastin of the skin can increase (Ashcroft et al, Age-related changes in the temporal and spatial distributions of fibrillin and elastin mRNAs and proteins in acute cutaneous wounds of healthy humans, J. Pathol., 1997, 183: 80-89). In the newly-born, the microfibrils are not all completely covered with elastin, and become so towards puberty. At 40 years, inclusions are seen to appear on the fibers, more frequently in women, and then the fragmentation of the elastic fibers and their disappearance under the dermal-epidermal junction (DEJ). This fractioning and/or this disappearance under the DEJ manifests itself by a loss of elasticity of the skin and the formation of wrinkles. The synthesis of non-functional elastic fibers is observed during photo-ageing, but this increase is accompanied with an accelerated loss of the elastic fibers under the DEJ. (Watson et al., Fibrillin-rich microfibrils are reduced in photo-aged skin. Distribution at the dermal-epidermal junction, J. Invest. Dermatol., 1999, 112: 782-787).

Furthermore, the neosynthesis of elastic fibers is carried out little in the scars of adult persons, while paradoxically, this property be in part found again in aged persons (more than 70 years old) whose elastic fibers produced are very fragmented. Yet the main components which intervene in the final composition of the elastic fibers are present (elastin, microfibrils) and the overall lysyl oxidase activity is maintained (Pasquall-Ronchetti and Baccarani-Contri, Elastic fiber during development and aging, Microscopy Res. Tech., 1997, 38: 428-435). This suggested to the inventors that one or more factors were missing which enable the formation of functional elastic fibers in the adult, but which exist during embryonic development and during the first age.

The prior art does not enable providing criteria which enable evaluating the impact of an active principle in dermato-cosmetology on a functional neo-elastogenesis. In this context, it is also very difficult to obtain objective criteria enabling the impact of these actives to be judged. The screening methods of actual active principles bear upon the evaluation of the expression of the genes involved in the formation of the elastic fibers, such as elastin or the fibrillins.

Furthermore, at the present time, animal experimentation is forbidden in cosmetics in Europe and human experimentation is ethically disputed. It is therefore unacceptable to the inventors to carry out a screening method, for cosmetic applications, which makes use of animals or human beings.

In three-dimensional models, such as Mimeskin® (Coletica, Lyons, France), keratinocytes induce the synthesis of tropoelastin and the deposit of tropoelastin on the microfibrils (Duplan-Perrat et al., Keratinocytes influence the maturation and organization of the elastin network in a skin equivalent. J. Invest. Dermatol. 114: 365-70, 1999). In the Mimeskin® model, the extracellular matrix showed an ultra-structural organization similar to that of the skin, with the collagen being organized in rays and elastic fibers which are constituted of elastin deposited on the microfibrils. This model has also been used for testing the effectiveness of certain molecules, such as inhibitors of lysyl oxidases. This has enabled proving that the inhibition of the lysyl oxidases induced a disorganization of the collagen fibers and the elastin fibers, but also a deviation from the program of differentiation of the keratinocytes, with a reduction of the level of expression of the labels of terminal differentiation, such as filaggrin (Farjanel et al., French patent 01 10443, CNRS, Use of inhibitors of lysyl oxidases for cell culture and tissue engineering (« *Utilisation d'inhibiteurs des lysyl oxydases pour la culture cellulaire and le genie tissulaire* »). In that patent, no distinction is made between the different Isoforms of LO.

However, those studies did not enable developing a method of identifying active principles which enable stimulating the formation of functional elastic fibers.

The prior art does not therefore enable providing active principles which enable stimulating the formation of functional elastic fibers.

Furthermore, the prior art does not enable a dynamic tracking of the zone of expression of the isoform of the lysyl oxidase LOXL, notably due to the fact that the methods provided by the prior art are Imprecise.

AIMS OF THE INVENTION

The aim of the invention is mainly to solve the technical problems set forth above and notably the technical problem aiming to provide a method of identifying active principles which stimulate the formation of functional elastic fibers. By "functional elastic fibers" is meant the usual meaning in the art as described above and notably in the context of the invention, elastic fibers which have elastic properties coming from a tridimensional structure.

The invention also relates to the use of the L isoform of lysyl oxidase or of an active principle which stimulates the enzymatic activity or the expression of the L isoform of lysyl oxidase (LOXL), notably for stimulating the formation of functional elastic fibers.

The invention enables solving the technical problem consisting of providing a method of locating the expression of LOXL and of tracking this expression.

SUMMARY OF THE INVENTION

In this text, by the term "LOXL", or "hLOXL", the inventors mean the L isoform of the human lysyl oxidase protein LOXL.

In this text, by the term "LOX", or "hLOX", the inventors mean the initial isoform of the human lysyl oxidase protein LOX.

By "stimulating the expression of the isoform of the lysyl oxidase LOXL", the inventors mean the stimulation of the expression of the gene encoding LOXL or of Its promoter, and notably the stimulation of the synthesis of the messenger RNA encoding LOXL, but also the stimulation of the synthesis of LOXL from this messenger RNA.

By "stimulating the expression of elastin", the inventors mean the stimulation of the expression of the gene encoding the elastin protein or of its promoter, and notably the stimulation of the synthesis of the messenger RNA encoding the elastin protein, but also the stimulation of the synthesis of the protein elastin or of its precursor, tropoelastin, from this messenger RNA.

In this invention, the inventors thus aim to stimulate mainly either the expression of LOXL as described, or the enzymatic activity of LOXL.

This stimulation must be effective enough to enable stimulating the formation of functional elastic fibers.

Active principles are considered as effective which enable obtaining an activation or an increase of about 1.5 times the expression and/or the activity of LOXL on a model, which comprises at least one cell type which presents an expression and/or an activity of LOXL, upon contact of these active principles, with respect to the level of expression and/or of activity of LOXL in a control model (without placing the active principles in contact).

It is such that the present invention relates, according to a firsts aspect, to the use of the « like » isoform of lysyl oxidase having the Sequence ID No 1, also called LOXL, or of an homologous or essentially homologous form thereof, or of a substance which promotes the activity and/or the expression of LOXL, for the manufacture of a composition for stimulating the formation of elastic fibers.

By "an homologous or essentially homologous form thereof" it is meant an homologous form of the isoform of lysyl oxidase LOXL which has the same or similar activity as LOXL as defined herein.

Advantageously, the expression of LOXL is either the expression of a sequence of nucleotides encoding LOXL or the expression of a sequence of peptides constituting a fraction of the protein LOXL, said sequence of peptides being preferably selected from the Sequence ID No 1.

Advantageously, said composition is a cosmetic, neutraceutical, medical or pharmaceutical composition.

Advantageously, the composition further comprises a second substance which stimulates the expression of the protein elastin, notably for stimulating the formation of elastic fibers, said second substance preferably being the substance which promotes the activity and/or the expression of LOXL.

Advantageously, said active substance comprises a region which fixes to at least one part of the sequence of nucleotides of the promoter of the human LOXL gene (Pr) (SEQ ID No 3) or of an homologous or essentially homologous form thereof, or modulates the expression of a protein which fixes to at least one part of the sequence of nucleotides of the promoter of the human LOXL gene (Pr) (SEQ ID No 3) or of an homologous or essentially homologous form thereof. This sequence is given from the nucleotide −2630 before the ATG codon, and the nucleotides from −2172 to −1 have in particular been studied.

Advantageously, the active substance is selected from the group consisting of dill, currant, cardamon, black radish, box holly, cinnamon, lactic bacteria-based fermentations, oats, potato, silk, Asa foetida gum, ethyl hexenoate and its derivatives, methyl butyrate and its derivatives, and ethyl decadienoate and its derivatives.

Advantageously, the use described above is carried out for inducing a neo-elastogenesis of the tissues, and notably for stimulating the elasticity of the tissues thus obtained, and for reducing skin wrinkles.

Advantageously, the use described above is carried out for combating against the loosening of the tissues, notably when the loosening of the tissues is observed during ageing or during solar exposures, for densifying the extracellular matrix, for firming up the subcutaneous tissues, for reducing skin wrinkles, for exerting an anti-wrinkles effect, for improving the quality of scar tissue and the appearance of scars, notably dystrophic and keloid scars, or for combating against stretch marks.

According to a second aspect, the invention relates to a cosmetic composition which comprises an active substance as defined above, optionally in a mixture with a cosmetically acceptable excipient.

According to a third aspect, the invention relates to a neutraceutical composition which comprises an active substance as defined above, optionally in a mixture with an excipient acceptable for food.

According to a fourth aspect, the invention relates to a pharmaceutical composition which comprises an active substance as defined above, optionally in a mixture with a pharmaceutically acceptable excipient.

For the cosmetic or pharmaceutical compositions, the excipient contains for example at least one compound selected from the group consisting of preservatives, emollients, emulsifiers, surfactants, moisturizers, thickeners, conditioners, matifying agents, stabilizers, antioxidants, texture agents, brightening agents, filmogenic agents, solubilisers, pigments, dyes, perfumes and solar filters. These excipients are preferably selected from the group consisting of amino acids and their derivatives, polyglycerols, esters, polymers and derivatives of cellulose, lanolin derivatives, phospholipids, lactoferrins, actoperoxidases, sucrose-based stabilisers, E vitamins and its derivatives, natural and synthetic waxes, plant oils, triglycerides, insaponifiables, phytosterols, plant esters, silicones and its derivatives, protein hydrolysates, jojoba oil and its derivatives, lipo/hydrosoluble esters, betaines, aminoxides, plant extracts, esters of sucrose, titanium dioxides, glycines, and parabens, and more preferably from the group consisting of butylene glycol, steareth-2, steareth-21, glycol-15 stearyl ether, cetearyl alcohol, phenoxyethanol, methylparaben, ethylparaben, propylparaben, butylparaben, butylene glycol, natural tocopherols, glycerol, sodium dihydroxycetyl, isopropyl hydroxycetyl ether, glycol stearate, triisononaoine, octyl cocoate, polyacrylamide, isoparaffin, laureth-7, a carbomer, propylene glycol, glycerol, bisabolol, dimethicone, sodium hydroxide, PEG 30-dipolyhydroxysterate, capric/caprylic triglycerides, cetearyl octanoate, dibutyl adipate, grape seed oil, jojoba oil, magnesium sulphate, EDTA, cyclomethicone, xanthan gum, citric add, sodium lauryl sulphate, mineral waxes and oils, isostearyl isostearate, propylene glycol dipelargonate, propylene glycol isostearate, PEG 8 Beeswax, hydrogenated palm tree heart oil glycerides, hydrogenated palm oil glycerides, lanolin oil, sesame oil, cetyl lactate, lanolin alcohol, castor oil, titanium dioxide, lactose, sucrose, low density polyethylene, and an isotonic saline solution.

Advantageously, the compositions cited above are formulated in a form selected from the group consisting of a solution, which is aqueous or oily, an aqueous cream or gel or an oily gel, notably in a pot or in a tube, notably a shower gel, a shampoo; a milk; an emulsion, a microemulsion or a nanoemulsion, notably an oil-in-water or water-in-oil or multiple or silicone-containing microemulsion or nanoemulsion; a lotion, notably in a glass bottle, a plastic bottle or in a measure bottle or in an aerosol; an ampoule; a liquid soap; a dermatological bar; an ointment; a foam; an anhydrous product, preferably a liquid, pasty or solid anhydrous product, e.g. in the form of a stick, notably in the form of a lipstick.

Advantageously, the compositions which are sufficiently liquid can be administered, notably via the parenteral, ocular, pulmonary, oral or nasal route.

Advantageously, the pasty or dry compositions (pastes, powders, tablets, capsules, granules, suppositories . . . ), can be introduced into the body notably via the oral, sublingual, nasal or rectal route.

Advantageously, when the formulation of the composition allows it, the administration route is cutaneous or transmucosal, notably by application of the composition on the skin or on a mucous membrane.

Advantageously, from the various formulations and routes of administration, the person skilled in the art will select the one which is adequate for the effectiveness sought after.

According to a fifth aspect, the invention relates to a method of cosmetic care characterized in that it comprises the use of a composition described above.

Advantageously, the cosmetic, care is selected from the group consisting of combating against the loosening of the tissues, notably when the loosening of the tissues is observed during ageing or during solar exposures, densifying the extracellular matrix, firming up the subcutaneous tissues, reducing skin wrinkles, anti-wrinkles effects, improving the quality of scar tissue and the appearance of scars, notably dystrophic and keloid scars, and combating against stretch marks.

According to a sixth aspect, the invention relates to a screening method of a substance which promotes the activity of LOXL or of an homologous or essentially homologous form thereof, for stimulating the formation of elastic fibers, characterized in that it comprises:

placing a potentially active substance in contact with LOXL at least one type of cells capable of expressing the isoform LOXL or of an homologous or essentially homologous form thereof, and a) analyzing the activity of LOXL or of an homologous or essentially homologous form thereof, notably with the aim of identifying whether said potentially active substance stimulates the activity of LOXL or of an homologous or essentially homologous form thereof, or b) analyzing the expression of LOXL or of an homologous or essentially homologous form thereof, notably with the aim of identifying whether said potentially active substance stimulates the expression of LOXL or of an homologous or essentially homologous form thereof.

Within the context of analyzing the expression of LOXL or of an homologous or essentially homologous form thereof:

Advantageously, it is sought whether said potentially active substance stimulates:

the expression of at least one sequence of nucleotides encoding the protein LOXL or of an homologous or essentially homologous form thereof, and/or the expression of a sequence of peptides essentially constituting a peptide fraction of the protein LOXL or of an homologous or essentially homologous form thereof.

Advantageously, the analysis of the expression of LOXL is carried out by qualitative and/or quantitative analysis of the expression of at least one part of a sequence of nucleotides encoding LOXL.

Advantageously, the sequence of nucleotides is the cDNA which is complementary to the mRNA encoding LOXL, the LOXL cDNA being defined by the sequence ID No 2.

Advantageously, the analysis of the expression of LOXL makes use of a reverse transcription polymerase chain reaction (RT-PCR) which comprises the use of primers which hybridize with at least one part of the sequence of nucleotides of the complementary DNA encoding LOXL (SEQ ID No 2), in order to amplify at least one part of the sequence of nucleotides encoding the LOXL.

Advantageously, the method also comprises a step locating the expression of LOXL which is carried out on a reconstructed skin model or on a a model based on biopsies:

by in situ hybridization, notably of at least one part of a sequence of nucleotides encoding LOXL for example by using at least one DNA probe which hybridizes with at least one part of the sequence of nucleotides of the complementary DNA encoding LOXL (SEQ ID No 2); or by immuno-detection notably by using at least one specific antibody of the LOXL.

The specific antibodies are itemized in Example 1.

Advantageously, the screening method comprises the comparison of the expression of LOXL with the expression of LOXL expressed in a control which does not comprise said potentially active substance.

Advantageously, the living cells comprise fibroblasts, originating notably from normal human skin, such as, for example, originating from the foreskin or from a skin of an adult subject.

Advantageously, the living cells comprise epithelial cells, for example keratinocytes, originating notably from normal human skin, such as, for example, originating from the foreskin or from a skin of an adult subject.

Advantageously, the living cells originate from at least one skin having a particular localization, for example from the face, from the abdomen, or from the breasts, and being able to be characterized as being «aged» or as being «exposed» to sun's radiation or not, or from a skin originating from a zone which has scars or stretch marks.

Advantageously, the screening method makes use of a reconstructed skin model, preferably at least one dermis model which comprises fibroblasts, or a model based on biopsies.

Advantageously, the screening method makes use of a reconstructed skin model or a model based on biopsies. The reconstructed skin model used is advantageously the Mimeskin® reconstructed skin model but may also be a model of connective matrix, of epidermis or of epithelium, or of reconstructed skin or mucous Membrane:

1) The Three-Dimensional Connective Matrix (Dermis or Chorion) Culture Model, comprises a support which is sown with stromal cells in order to form reconstructed dermis or reconstructed chorions. This support is preferably selected from:
 an inert support selected from the group consisting of a semi-permeable synthetic membrane, in particular a semi-permeable nitrocellulose membrane, a semi-permeable nylon membrane, a Teflon membrane or a Teflon sponge, a semi-permeable membrane of polycarbonate or polyethylene, polypropylene, or of polyethylene terephthalate (PET), a semi-permeable Anopore inorganic membrane, of cellulose acetate or cellulose ester (HATF) membrane, a semi-permeable Biopore-CM membrane, a semi-permeable polyester membrane, a membrane or a film of polyglycolic acid. In this group; the dermal models Skin$^2$™ model ZK1100 and Dermagraft® and Transcyte® (Advanced Tissue Sciences) for example, are found;
 a cell culture-treated plastic (formation of a dermal leaf: Michel M. et al. in In Vitro Cell. Dev Biol.-Animal (1999) 35: 318-326);
 a gel or a membrane based on hyaluronic add (Hyalograft® 3D—Fidia Advanced Biopolymers) and/or on collagen and/or on fibronectin and/or on fibrin; in this group, dermal model Vitrix® (Organogenesis) for example is found;
 a porous matrix; which is surfaced or non-surfaced, made from collagen being able to contain one or more glycosaminoglycans and/or eventually chitosan (EP 0 296 078 A1 of the CNRS, WO 01/911821 and WO 01/92322 of Coletica).

2) The Three-Dimensional Epidermis or Epithelium Culture Model

Comprises a support which is sown or not beforehand with stromal cells, particularly fibroblasts, and then with epithelial cells and in particular keratinocytes, so as to obtain reconstructed epithelia or epidermis. This support is preferably selected from:
 an inert support selected from the group, consisting of a semi-permeable synthetic membrane, in particular a semi-permeable nitrocellulose membrane, a semi-permeable nylon membrane, a Teflon membrane or a Teflon sponge, a semi-permeable membrane of polycarbonate or polyethylene, polypropylene, or of polyethylene terephthalate (PET), a semi-permeable Anopore inorganic membrane, of cellulose acetate or cellulose ester (HATF) membrane, a semi-permeable Biopore-CM membrane, a semi-permeable polyester membrane; in this group, the reconstructed models Epiderm and Epithelia (Skinethic®) are found, as well as the models EpiDerm®, EpiAirway®, EpiOccular® (Mattek Corporation); a film or a membrane based on hyaluronic acid and/or on collagen and/or on fibronectin and/or on fibrin. In this group, the models: Episkin® (L'Oreal) and Laserskln® (Fidia advanced Biopolymers), in particular, can be cited.

3) The Three-Dimensional Reconstructed Skin or Mucous Membrane Culture Model

Comprises a matrix support (dermal or of chorion) which is sown with epithelial cells so as to obtain a reconstructed mucous membrane or with keratinocytes so as to obtain a reconstructed skin. This support is preferably selected from:
 an inert support selected from the group consisting of a semi-permeable synthetic membrane, in particular a semi-permeable nitrocellulose membrane, a semi-permeable nylon membrane, a Teflon membrane or a Teflon sponge, a semi-permeable membrane of polycarbonate or polyethylene, polypropylene, or of polyethylene terephthalate (PET), a semi-permeable Anopore inorganic membrane, of cellulose acetate or cellulose ester (HATF) membrane, a semi-permeable Biopore-CM membrane, a semi-permeable polyester membrane, said inert support containing stromal cells, in particular fibroblasts,
 a gel based on collagen and/or hyaluronic acid and/or fibronectin, and/or on fibrin comprising stromal cells, in particular fibroblasts,
 a porous matrix, which is surfaced or non-surfaced, made from collagen being able to contain one or more glycosaminoglycans and/or eventually chitosan, these porous matrices integrating stromal cells, in particular, fibroblasts,
 a human or animal de-epidermisised dermis or dead dermis.

In this group, the models Apligraf® (Organogenesis), ATS-2000 (CellSystems® Biotechnologie Vertrieb), as well as Skin$^2$™ (ZK1200-1300-2000—Advanced Tissue Science), in particular, can be cited.

Furthermore, models exist which are dedicated to tissue therapy and which can also be the subject of such studies. The models Epidex™ (Modex Thérapeutiques), Epibase® (Laboratoire Genevrier), Epicell™ (Genzyme), Autoderm™ and Transderm™ (Innogenetics), can be cited.

Advantageously, the screening method makes use of a reconstructed skin model, preferably at least one epidermis model which comprises keratinocytes.

Advantageously, the method comprises a step of analyzing the expression of a sequence at least of the protein elastin and/or tropoelastin, or of a sequence of nucleotides encoding the protein elastin, notably for detecting an eventual stimulation of the expression of the protein elastin when said active substance is in contact with said living cells.

Advantageously, the method comprises a step of immuno-detecting the expression of the protein LOXL, notably with the aim of performing the traceability of neo-elastogenesis, notably in the epithelial tissues and/or in the connective tissues, said tissues originating from at least one reconstructed skin model or from a model based on biopsies.

Advantageously, said active substance is selected from the group consisting of dill, currant, cardamon, black radish, box holly, cinnamon, lactic bacteria-based fermentations, oats, potato, silk, Asa foetida gum, ethyl hexenoate and its derivatives, methyl butyrate and its derivatives, and ethyl decadienoate and its derivatives.

According to a seventh aspect, the invention relates to a method of locating the expression of LOXL or of an homologous or essentially homologous form thereof in tissues with the aim of performing the traceability of neo-elastogenesis, notably in connective tissues, said tissues originating from at least one reconstructed skin model or from biopsies, characterized in that the method comprises a step of immuno-detecting the protein LOXL or of an homologous or essentially homologous form thereof or of in situ hybridizing at least one part of a sequence of nucleotides encoding LOXL or of an homologous or essentially homologous form thereof.

The invention also relates to a method of locating the expression of LOXL in tissues with the aim of performing the traceability of neo-elastogenesis, notably in epithelial tissues and/or in connective tissues, characterized in that the method comprises a step of immuno-detecting the protein LOXL or of in situ hybridizing the gene encoding LOXL.

The invention also relates to the use of an active principle which modifies the enzymatic activity or the expression of the protein LOXL for stimulating the formation of elastic fibers.

The invention also relates to a method of treatment of a deficiency associated with the enzymatic activity of the isoform of the protein lysyl oxidase LOXL which comprises administering, to a subject, a therapeutically effective amount of a composition which comprises the protein lysyl oxidase LOXL, or of an homologous or essentially homologous form thereof, or a compound which stimulates the enzymatic activity or the expression of the protein lysyl oxidase LOXL.

Advantageously, this method of treatment enables performing a treatment selected from combating against the loosening of the tissues, notably when the loosening of the tissues is observed during ageing or during solar exposures, densifying the extracellular matrix, firming up the subcutaneous tissues, reducing skin wrinkles, anti-wrinkles effects, improving the quality of scar tissue and the appearance of scars, notably of dystrophic scars, in particular dystrophic scars, and keloid scars, and combating against stretch marks.

DETAILED DESCRIPTION OF THE INVENTION

The inventors have unexpectedly demonstrated that the activity of LOXL was a main missing link in elastogenesis in the adult and that it was possible to reactivate the synthesis of this isoform of lysyl oxidase so as to obtain a stimulating effect on elastogenesis.

The inventors have in fact demonstrated that this isoform of the family of lysyl oxidases (LO) is associated with elastogenesis in a reconstructed skin model producing elastic fibers. In seeking whether this isoform was present or absent in the skin of various ages and during skin alterations, the inventors noticed the simultaneous presence or absence of this isoform and of elastogenesis, and this enables indicating that the activity of this isoform of LO corresponds to a missing link the synthesis of which is necessary to modulate in order to orchestrate a functional elastogenesis.

The inventors have thus developed a method which enables visualizing increased expressions of this isoform of LO (LOXL), and then have sought active principles, notably amongst plant extracts or chemical molecules, which in particular stimulate the expression of the mRNAs encoding LOXL. The actives selected were then incorporated in cosmetic, dermo-pharmaceutical and pharmaceutical compositions in particular, for applications in the combat against loosening of the tissues during ageing, as well as in the improvement of the quality of scar tissue and the appearance of scars and stretch marks.

The inventors have developed specific antibodies of the mature LOXL forms (vide Examples 1 and 2), and have demonstrated in this way that the absence of this lysyl oxidase isoform is correlated to the problems of the synthesis of functional elastic fibers, notably during ageing of the skin tissues, whether they be natural or induced by solar radiation.

The isoforms LOXL2, LOXL3 and LOXL4 are not or are little expressed in the dermis and are not involved in elastogenesis (vide Example 4). The LOX isoform is present in the dermis and can be associated with the microfibrils, but LOX is involved in the formation of the functional collagen fibers and is not missing in adult skins. The absence of LOX is therefore not correlated with the loss of elasticity of the elastic fibers during ageing (vide Example 3).

This demonstration of the role of LOXL in elastogenesis was crucial for the implementation of the present invention (vide Example 5).

The association between LOXL and the elastic fibers or the microfibrils was clearly demonstrated by electron microscopy during the implementation of the present invention. LOXL associated with the microfibrils constitutes the framework on which the elastin is deposited.

LOXL is the enzyme which is responsible for the maturation of the elastin by cross-linking and thus enables the formation of functional elastic fibers.

Within the context of the present invention, the inventors have implemented a method of locating the expression of LOXL.

Notably, this method of location comprises the immuno-detection of LOXL. It is also possible by this method to demonstrate the expression of the protein elastin. It has been demonstrated by the inventors studies that LOXL is detected in association with the dense deposits or on the microfibrils, but not with the collagen fibers. Elastin was detected in the same dense deposits and in the microfibrils. This detection is made on reconstructed skin models, and notably on reconstructed skin models 30 days after the application of the keratinocytes (vide Example 5).

The association of LOXL with the microfibrils and with the elastic fibers was also confirmed on the skin of the foreskin, notably by transmission electron microscopy after immuno-detection.

LOXL is expressed in the dermis of the skin of the foreskin taken from young, patients (a few months), which have still a large synthesis of elastin. LOXL is not however expressed in the dermis of the skin, of the neck, of the breast, of the abdomen or of the face of adult persons. This absence of detection of LOXL in the dermis of the skin of the neck, of the breast, of the abdomen, or of the face, is confirmed in the adult whatever the age. A high expression was also observed of LOXL in the epidermis of human skin, with however a late extinction of the expression of this enzyme when the human skins originate from subjects aged about 80 years old and more (vide Example 6).

With regard to scars, LOXL was not observed in the dermis of these zones, neither three months after the scar, nor five years after the formation of the scar.

In this context, it is to be noted that the elastin which was present at three months is no longer present on this scar tissue zone five years after the formation of the scar.

The inventors have thus demonstrated the role of LOXL in the formation of elastic fibers, notably by using reconstructed skin models or dermis of the foreskin of young patients.

The inventors have also demonstrated the deficit of expression of LOXL in the scar tissue zones, as well as in the dermis of human skin of varying age, thus during ageing.

Amongst the isoforms of the lysyl oxidases, LOXL is one of the isoforms which enables the cross-linking of the elastic fibers. However, only this isoform, LOXL, is missing in the adult for the cross-linking of the elastic fibers enabling functional fibers to be obtained.

The inventors have, from these unexpected discoveries, carried out a screening method of an active principle which stimulates the formation of functional elastic fibers with the view to identifying active principles for making cosmetic or pharmaceutical compositions.

The present invention further relates to the activation of the promoter of the human gene encoding LOXL (vide Example 7). Various zones of activities of this promoter have been demonstrated.

The sequence of this promoter is given in the annex and is designated in the following text by PrhLOXL.

On this promoter, the region corresponds to the nucleotides −712/−391 (according to the numbering defined from +1 of translation of the hLOXL gene) which possesses an up-regulating activity on the reporter gene luciferase, which is expressed for example after transitional transfection in fibroblasts of the skin of the human foreskin.

The inventors have been able to define putative sites of regulation by nuclear factors. These factors have been correlated to cytokines or other factors known to act upon the transcription of certain genes.

Various regions of PrhLOXL have been able to be identified as being activating or inhibiting zones.

Notably, the regions −2172/−2002; −1438/−968; −712/−391; have been located as being activating regions; and the regions: −2002/−1438; −968/−712 have been identified as being inhibiting regions. The −80/−1 region is not active and is situated down from +1 of transcription. In this numbering, the putative transcription +1 is situated in position −342 with respect to the site of initiation of the translation. In this way, several sites of these regions have been shown which are susceptible to regulating the hLOXL gene. These sites are notably two putative sites of response to retinoic acid, two putative sites of response to TGF-β (Transforming Growth Factor β), a putative site of response to EGF (Epidermal Growth Factor), three putative sites of response to oestrogens and two putative sites of response to glucocorticoids (GRE).

This implies that the active principles which stimulate the neo-synthesis and/or the activity of hLOXL and thus which stimulate the formation of elastic fibers which act upon the promoter of the hLOXL gene, and notably in these zones, either directly or indirectly, in modulating the expression of a protein fixing onto these sites. It will therefore be possible for a substance to be considered as active when it will comprise a region which is capable either of associating with at least one part of the sequence of nucleotides of PrhLOXL, and in particular of associating with the putative sites defined above, or of modulating the expression of a protein which is capable of doing it.

The whole of the inventors' studies has enabled developing a method of identifying an active Principle which stimulates the formation of elastic fibers.

Within the context of the present invention, the inventors have implemented an in situ hybridization which thus enables locating and verifying the presence of the expression of the messenger RNAs which encode LOXL in particular. This in situ hybridization is notably carried out by double strand DNA probes which are labeled with digoxigenin on sections of reconstructed skin models obtained 30 days after the addition of keratinocytes, and included in paraffin. This in situ hybridization was also carried out in order to verify the expression of the messenger RNAs of tropoelastin and of collagen α1(I) (vide Example 8).

The expression of the LOXL mRNAs is positive in the deep dermis and throughout the whole epidermis. The expression of the tropoelastin mRNA is located near to the dermal fibroblasts and in the epidermis. The expression of the collagen Iα1 mRNA is located in the dermis but not in the epidermis. This enables, within the context of the present invention, locating and verifying the presence of the expression of the LOXL mRNAs, notably in a reconstructed skin model, for example after application of an active principle which stimulates the formation of functional elastic fibers.

Within the context of the present invention, the hLOXL gene was activated by the addition of keratinocytes in a reconstructed skin model, and notably in the reconstructed skin model Mimeskin®, (Coietica, Lyons, France). The induction of the synthesis of the LOXL mRNAs is concomitant notably with that of tropoelastin, and notably appears about 6 days after the addition of the keratinocytes on the dermis equivalent.

The present invention has also enabled demonstrating the decrease in the level of expression of notably the hLOXL gene, as well as of the human elastin gene, in fibroblasts originating from aged donors.

For this, the inventors used 5 strains of fibroblasts from the foreskin (FF) (originating from young infants) and 6 strains of adult fibroblasts (AF, of which 3 subjects of 20 years old on average, and 3 subjects of 60 years old on average) originating from plastic surgery on the abdomen. The expression of the gene encoding the protein LOX was also tested (vide Example 9).

The expression of these 3 genes of interest, as well as the one of actin, was analyzed by real time RT-PCR. The invention is not limited to this type of analysis. This technique enables precisely quantifying the expression of a gene in comparing it to that of actin which is considered to be constant. The regulation of the level of expression of this gene can therefore be quantified.

Figure 12:
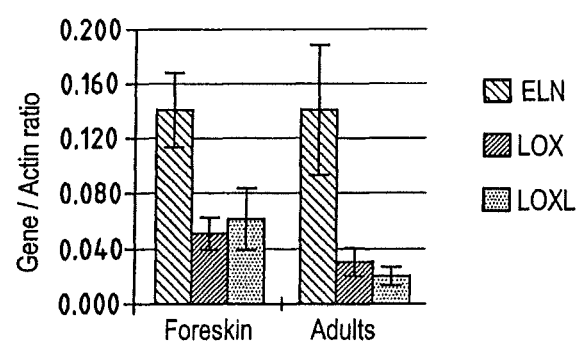

The results presented in FIG. 12 first of all show that the synthesis of LOXL mRNA drops spectacularly and statistically significantly in the fibroblasts of adults, with a drop of near to 70% with respect to the fibroblasts of the foreskin, whereas the elastin mRNA does not vary significantly with age. This piece of data is in agreement with the literature on elastin, since if the elastic tissue deteriorates and is not replaced, it does not seem to be due to an inhibition of the activity of the elastin gene.

The synthesis of LOX mRNA decreases on average by 40% in the AFs with respect to the FFs, but since this enzyme is not always expressed in normal human skin, this variation is not very indicative of the phenomena in vivo.

It is advantageous to also stimulate the expression of elastin so as to stimulate the formation of elastic fibers even more.

The present invention provides a method enabling identifying the expression of LOXL, notably in fibroblasts.

The present invention has aimed to implement these various techniques in a way as to identify active principles stimulating the formation of elastic fibers.

In general, the methods of the present invention implement seeking the expression of the protein LOXL, and notably seeking the expression of the messenger RNAs encoding LOXL (vide Example 10).

The invention also relates to the active principles which stimulate the formation of elastic fibers (vide Examples 11 and 12).

The invention also relates to the use of the enzyme LOXL, or of a derivative form, or of the active principles as described above, for making cosmetic or pharmaceutical compositions (vide Examples 13 to 18). The stimulation of LOXL can be carried out at gene level, of the messenger RNA, or of the protein directly. This activation enables the formation of elastic fibers, notably by virtue of the cross-linking of the elastin by the enzyme LOXL.

Other aims, features and advantages of the invention will appear clearly to the person skilled in the art upon reading the explanatory description which makes reference to the following Examples.

The Examples make up an integral part of the present invention and any feature appearing novel with respect to any prior state of the art from the description taken in its entirety, including the Examples, makes up an integral part of the invention in its function and in its generality.

Thus, every Example is of general scope.

Furthermore, in the Examples, all the percentages are given by weight, unless indicated otherwise, the temperature is expressed in degrees Celsius unless indicated otherwise, and the pressure is atmospheric pressure, unless indicated otherwise.

EXAMPLES

Example 1

The invention has first of all covered the development of novel specific antibodies of LOX and LOXL but which are capable of detecting their mature forms. The antibodies were developed against the mature regions of LOX and LOXL. The antigenic regions were selected in order to present the minimum of similarity with the corresponding regions on the other isoforms of the lysyl oxidases (LOS). The antibodies obtained against the regions of the peptides $LOX^{V228-S280}$ were called anti-LOXmat and similarly for the antibodies obtained against the region of the peptides $LOXL^{R231-G368}$ called anti-LOXLpro.

In FIG. 1: Description of the Sequences of the LO Defined for Giving the Specific Antibodies:

This figure represents the steps which have led to the selection of the antigenic regions in order to develop the anti-LOX and anti-LOXL antibodies.

FIG. 1(A):

Schematic representation of hLOX (human LOX protein) and hLOXL (human LOXL protein).

The sequences of hLOX and hLOXL are indicated with open boxes, dotted in the C-terminal regions, in order to highlight the regions of high similarity. The position of the cleavage of the pre-region and of the site of cleavage by procollagen-C-proteinase (PCP), on the A22 and D169 residues of hLOX respectively, was indicated. The position of the cleavage of the pre-region of LOXL, before the Q26 residue, of the N-terminal maturation site of the 56 kDa precursor (before Q135), and the position of the cleavage sites by PCP of the LOXL precursor of 56 kDa (before the D 338 residues), are indicated. The corresponding LOXL proteins $Q^{26}$-$S^{574}$, $D^{135}$-$S^{574}$, and $D^{338}$-$S^{574}$ would display a deduced molecular mass of approximately 63 kDa, 54.6 kDa, and 26.7 kDa, respectively. The location of the recombinant peptides used for obtaining the anti-LOX antibodies were indicated: the G128-L212 peptide for the anti-LOXpro, the V228-S280 peptide for the anti-LOXmat, and the D305-N373 peptide for the anti-LOXcat. The location of the recombinant peptides used for developing the anti-LOXL antibodies were indicated: the R231-G368 peptide for the anti-LOXLpro and S355-D415 for the anti-LOXLmat.

FIG. 1(B) The percentage of similarity between the antigenic regions of LOX and LOXL with their equivalents on the LO isoforms was indicated in this Table.

In the Table of FIG. 1(B), hLOXL represents the human LOXL protein, bLOXL represents the bovine LOXL protein, mLOXL represents the mouse LOXL protein, hLOXL represent the human LOX protein, bLOX represents the bovine LOX protein; hLOXL2 represents the human LOXL2 protein, hLOXL3 represents the human LOXL3 protein, hLOXL4 represents the human LOXL4 protein.

The length column (aa) contains the value of the number of amino acids contained in the corresponding regions.

In order to obtain the antibodies, the chimeric genes were constructed by inserting the defined sequence of hLOXL or hLOX in phase with the gene of glutathion-S-transferase (GST), in the BamHI-XhoI sites of the expression plasmid pGEX-4T-3 (Amersham Biosciences).

The fusion gene GST-LOXL$^{S355-D415}$ was constructed by introducing the cDNA sequence of HLOXL (cDNA hLOXL), produced by PCR with the sense primer 5'-TTGGATC-CAGCGTAGGCAGCGTGTAC-3' (SEQ ID No 17), and antisense primer 5'-AAACTCGAGCATCGTAGTCG-GTGGC-3' (SEQ ID No 18).

The fusion gene GST-LOX$^{G128-L212}$ was constructed by introducing hLOX cDNA amplified with sense primer 5'-TCGGATCCGGCTACTCGACATCTAGAGCC-3' (SEQ ID No 18) and antisense primer 5'-GTCCTCGAGACCG-TACTGGAAGTAGCC-3' (SEQ ID No 19), respectively.

The fusion gene GST-LOX$^{V228-S279}$ was constructed by introducing the hLOX sequence amplified with sense primer 5'-TTGGATCCGTGCAGAAGATGTCCATGTAC-3' (SEQ ID No 20) and antisense primer 5'TTTCTCGAGGCTGGG-TAAGAAATCTGATG-3' (SEQ ID No 21), respectively.

The fusion gene GST-LOX$^{D306-N373}$ was constructed by introducing hLOX cDNA amplified with sense primer 5'CACTATGGATCCCTTGATGCCAACACCC-3' (SEQ ID No 22) and antisense primer 5'-CACGACCTTTAG-GATATCGTTTCCAGG-3' (SEQ ID No 23), respectively.

For the whole of these amplifications by PCR, the Taq polymerase High Fidelity (Roche Diagnostic, Meyman, France) was used.

The fusion proteins GST-LOX and GST-LOXL, as well as the rabbit polyclonal antibodies were obtained and purified as described above for the fusion proteins originating from the expression of the fusion genes GST-LOXL$^{S355-D415}$ and GST LOX$^{G128-L212}$ (Decitre et at., Lab Invest, 78: 143-151, 1998; Borel et al., J. Biol. Chem, 276: 48944-49, 2001).

For the adsorption experiments, the antibodies were incubated for 3 hours at 20° C. with the fusion proteins, themselves adsorbed on a nitrocellulose membrane, Hybond-ECL membrane (Amersham Biosciences) before the Immuno-detection.

These pieces of work have first of all enabled demonstrating the mature forms of LOX and LOXL, by virtue of the immunochemical and biochemical characterization of the mature proteins (vide Example 2, FIG. 2). The antibodies developed are distinguished from those used in the prior art for LOXL, which no not enable a recognition of the mature form of LOXL (Decitre et al., *Lab Invest* 78: 143-151, 1998; Borel et al., *J. Biol. Chem.*, 276: 48944-49, 2001). The invention has been to use the anti-LOXLmat antibody and anti-LOXmat antibody, and this enabled demonstrating a protein of 31 kDa, which is recognized by the anti-LOXLmat but not by the anti-LOXmat, and which corresponds to the mature form of LOXL. This part of the invention demonstrates a real progress over the prior art, notably with reference to the patent of Csiszar et al., which describes all the proteins originating from the genes of the LO family without defining the features of them (WO 01/83702 A2 patent application: Novel members of the lysyl oxidase family of amine oxidases related applications).

Example 2

Immuno-Detection of LOX and LOXL of Muscle Cells by Virtue of the Novel Antibodies Anti LOX and Anti-LOXL On FIG. 2:

FIG. 2 represents photographs of electrophoreses which were carried out as indicated below. These electrophoreses demonstrate the characterization of the mature proteins of LOX and LOXL, of smooth muscle cells (SMC) by virtue of the antibodies anti-LOX and anti-LOXL, identified in Example 1.

The proteins of the cell strain (L) and of the cell culture medium (M) of a cell line of rat smooth muscle (developed by Jean-Marie Daniel Lamaziere, Bordeaux) were extracted and detected by western blotting by using the antibodies anti-LOXLmat, anti-LOXmat, anti-LOXLpro and anti-LOXpro. The cells were cultivated at 37° C. in an atmosphere of 5% $CO_2$ in DMEM medium (Sigma) containing 10% foetal calf serum, 2 mM glutamine and 50 µg/ml gentamycin.

The cell strain proteins, which are washed twice with PBS buffer, were extracted for 2 hours at 4° C. with slow agitation in the lysis buffer (16 mM phosphate buffer pH 8, 0.5% NP40, protease inhibitors (Complete Mini, Roche Diagnostics), and urea 6 M). The lysates were diluted with two volumes of 16 mM phosphate buffer pH 8, with protease inhibitors (Complete Mini, Roche Diagnostics, Meylan, France), and centrifuged for 5 minutes at 15,000 g. The soluble proteins were precipitated by adding 10% trichloroacetic acid (TCA) before the electrophoresis.

The proteins of the culture media of cells cultivated for 48 hours without serum, are recovered, precipitated by adding 10% TCA or 50% saturated ammonium sulphate.

For the immuno-detection, the proteins are separated by 10% SDS-polyacrylamide gel electrophoresis. The proteins were transferred onto a polyvinylidene fluoride (PVDF) membrane (Immobilon P$^{SQ}$, Millipore) and were immuno-detected as described above (Borel et al., 2001).

The developed antibodies thus enable characterizing and locating the mature and immature forms of LOX and LOXL in the biological tissues.

Example 3

Demonstration of the Role of LOX and LOXL in Elastogenesis

The inventors have demonstrated that the LOX and LOXL proteins can be associated with the formation of connective tissue in the dermis of reconstructed skin models by immuno-histochemistry (FIG. 3). This demonstration was obtained without any ambiguity by virtue of the use of anti-LOX and anti-LOXL antibody couples, directed against the pro-enzymatic regions and mature regions of the two enzymes (LOX and LOXL).

On FIG. 3 representation is made of the immuno-histological detection of LOXL and LOX in the reconstructed skin (RS) and normal human skin.

The immuno-detection of LOXL (A, C, E, G) on the reconstructed skin at days 16 (A), 35 (C), and 45 (E), by using anti-LOXL$^{R231-G368}$ (A, C, E) or anti-LOXL$^{R231-G368}$ adsorbed with the corresponding peptide GST-LOXL$^{R231-G368}$ before the immuno-detection (G). The immuno-detection of LOX (B, D, F, H) at days 16 (B), 35 (D), and 45 (F), by using anti-LOX$^{V228-S279}$ (B, D, F) or anti-LOX$^{V228-S279}$ adsorbed with the corresponding peptide GST-LOX$^{V228-S279}$ before the immuno-detection (H). The immuno-detection of LOXL (I) and of LOX (J) in the skin of human foreskin is carried out by using anti-LOXL$^{R231-G368}$ (I) and anti-LOX$^{V228-S279}$ (J). The position of the dermal-epidermal junction is indicated with an open arrow, that of the dermal substrate with an arrow, and the location of the keratinocytes at day 16 is indicated with an arrow head.

The reconstructed skin (Mimeskin®, Coletica, Lyons, France) was prepared in Bouin's fixative (LOX, LOXL, elastin) or in a 10% formol solution (for the elastin), and then included in paraffin. 6 µm thick sections were ridded of paraffin and were whitened in glycine-HCl (100 mmol/l). The anti-LOX and anti-LOXL antibodies are described above.

The antibodies were used at the following dilution: 1:500 (anti-LOXL$^{R231-G368}$), 1:100 (anti-LOX$^{V228-S279}$, anti-LOXL$^{S355-D416}$). The immune complexes were detected with a rabbit (goat) anti IgG conjugated with peroxidase (DAKO, Trappes, France), by using diaminobenzidine as substrate (DAKO).

LOXL is thus an excellent candidate for participating in elastogenesis in a reconstructed skin model notably such as Mimeskin®.

Example 4

Demonstration of the Role of LOXL2, LOXL3, and LOXL4 in Elastogenesis

The invention also covers the development of two novel anti-LOXL2 antibodies, one of these antibodies theoretically also recognizing LOXL3 and LOXL4. This has enabled defining whether these enzymes are expressed with elastin in the dermis of a reconstructed skin model. The analysis by immuno-histochemistry by using the two anti-LOXL2 antibodies does in fact show that this antigen, as well as the two antigenically linked proteins LOXL3 and LOXL4, are not or are little expressed in the dermis, and that therefore, they do not participate in the elastogenesis.

Figure 4:
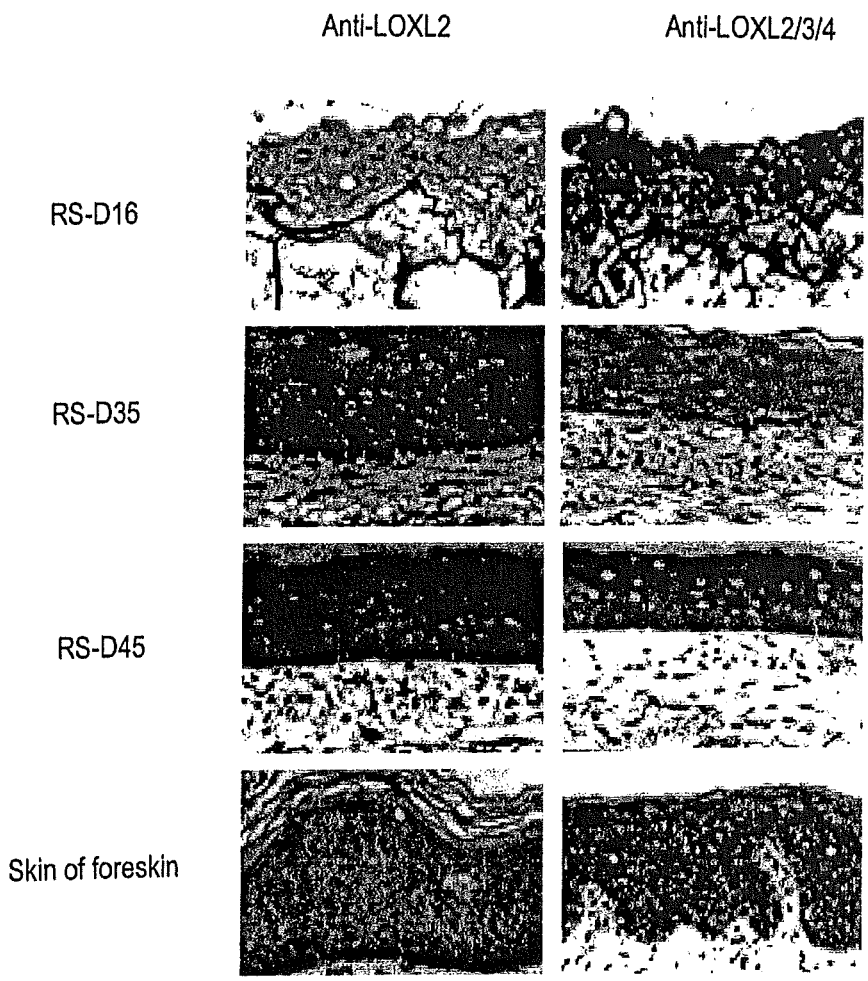

On FIG. 4: the Immuno-detection is represented on the sections of reconstructed, skin (16, 35 and 45 days) and of human foreskin skin with the antibody anti LOXL2$^{517-581}$ (left column) and the antibody anti-LOXL2$^{664-720}$ theoretically recognizing LOXL2, LOXL3, and LOXL4 (right column).

The anti-LOXL2 antibodies were obtained against fusion peptides GST-LOXL2, as described above (Decitre et al, Lab. Invest, 78, 143-151, 1998). The fusion gene GST-LOXL2$^{517-581}$ was constructed by introducing the sequence 1543 to 1747 of the human LOXL2 gene (hLOXL2) in the plasmid, as described above.

This segment was generated by PCR with the sense primer 5-GAGCTGGGATCCGCGCACTGCC-3' and antisense primer 5'-GGCTGAGTCGACGAGGCAGTTCTCC-3'.

The fusion gene GST-LOXL2$^{664-720}$ was constructed by introducing the corresponding hLOXL2 sequence, by virtue of the sense primer 5'-CACAGGATCCGAAGGAGACATC-CAGAAG-3' and antisense primer 5'-TTTCTGAGCTCCT-GCATTTCATGATG-3'.

The fusion proteins and the anti-rabbit antibodies generated against these proteins were prepared as described above. The antibody, against the 517-580 peptide was called anti-LOXL2, since this region is specific of LOXL2.

The antibody against the 664-734 peptide was called anti-LOXL-R (for «relative to»), since this region of LOXL2 possesses a high similarity with LOXL3 and LOXL4 (about 74.6% and 60.5%, respectively).

The reconstructed skins (Mimeskin®, Coletica, Lyons, France) at 16 days (RS-D16), 35 days (RS-D35) and 45 days (RS-D45), and the skin of the human foreskin are analyzed as above by immuno-histochemistry with the anti-LOXL2-R and anti-LOXL2 antibodies. Anti-LOXL2 shows an expression of LOXL2 in the epidermis and not in the dermis, while the antibody directed against the common C-terminal region of LOXL2, LOXL3, and LOXL4 confirms the expression of these enzymes in the epidermis and shows a low expression in the dermis but in an zone which does not correspond to the sites of elastogenesis.

LOXL2, LOXL3 and LOXL4 are therefore not involved in elastogenesis.

Example 5

Demonstration of the Role of LOXL in Elastogenesis

The association between LOXL and LOX on the one hand, and the elastic fibers or the microfibrils on the other, was clearly demonstrated in transmission electron microscopy by the present invention.

Figure 5:
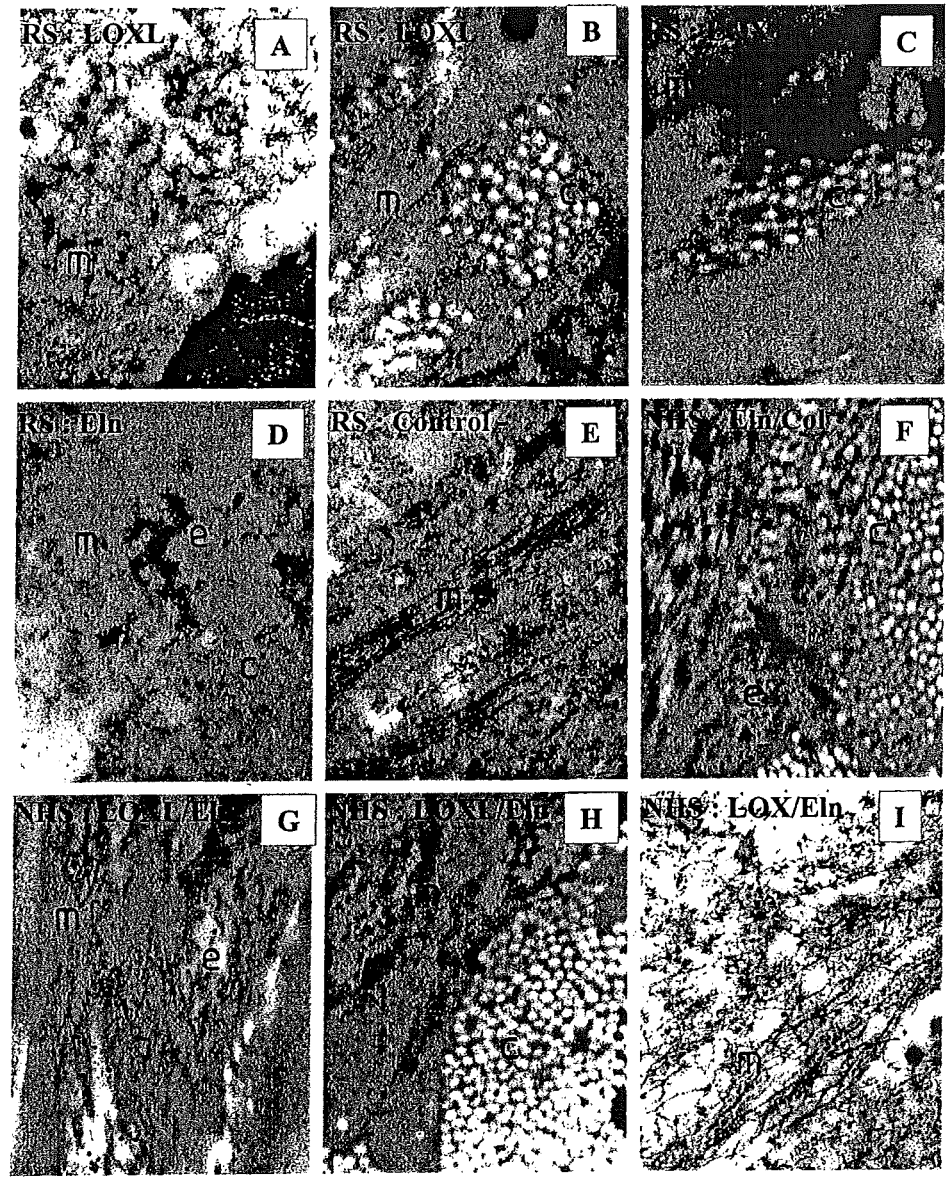

LOX and LOXL associated with the microfibrils constitute the framework on which the elastin is deposited, whereas only LOX is associated with the formation of the collagen fibers (vide FIG. 5).

On FIG. 5: The immuno-detection of LOXL, of LOX and of elastin is represented by transmission electron microscopy in the dermal part of the reconstructed skin 30 days after the application of the keratinocytes, and of the normal human skin.

The tissues were fixed for 3 hours at 4° C. with 4% paraformaldehyde in PBS buffer containing 0.1% glutaraldehyde, and were then washed in phosphate buffer containing 0.4M of sucrose cacodylate and O$_2$M lysine, dehydrated in solutions of ethanol, and included in LR White (Euromedex, France). The detection was carried out with primary antibodies diluted to 1:50 in Tris-HCl buffer at pH 8.2, to which 1% bovine serum albumin (BSA) is added. The immune complexes are detected with an rabbit anti-IgG antibody conjugated with colloidal gold particles of 10 and 20 nm (Biocell, Tebu, France) diluted to 1:40. The samples were contrasted with 3% aqueous uranyl acetate and lead citrate, and were then examined under a JEOL 1200 EX transmission electron microscope. The immuno-detection was carried out on the reconstructed skin (A-D) and on the skin of human foreskin (F-I).

On the reconstructed skin, it was carried out with the antibodies: anti-LOXL (A, B), anti-LOX (C), anti-elastin (Elm) (D), human anti-elastin antibodies being commercially available (Sigma, USA) and diluted to 1:50, and a negative control without primary antibody in the dermis (control) (E). A double labelling (F-I) was made on the skin of the human foreskin.

References A-D: Immuno-detection of LOXL, LOX and elastin by electron microscope in the dermal part of the reconstructed skins at 45 days.

Reference E: Positive control with anti-elastin and anti-collagen I antibodies in the dermis of reconstructed, skins at 45 days, i.e. 30 days after the addition of keratinocytes.

References F and I: Double immuno-detection of LOXL, LOX, elastin and collagen by electron microscopy in the dermal part of human foreskin.

References G-H: Double-labelling in the dermal part of the human foreskin with the rabbit anti-LOXL antibody (the rabbit anti-IgG is conjugated with 10 nm gold particles) and the murine anti-elastin antibody (the mouse anti-IgG is conjugated with 20 nm gold particles).

Keys in the Figure: m: microfibrils, c: collagen fibers, e: amorphous elastin. Bar of the scale: 500 nm.

LOXL (A-B) is detected in association with the dense deposits or on the microfibrils, but not with the collagen fibers which appear in white on these sections. The labelling of LOX (C) is low, although a few gold particles could be found with the dense deposits, the microfibrils and the collagen. The anti-elastin antibodies detected the same dense deposits and the microfibrils (D). The association of LOXL and LOX to the microfibrils and to the elastic fibers was confirmed in the skin of the human foreskin, by electron microscopy after immuno-detection (G-H). As in the observations on the reconstructed skin models, LOXL is not associated with the collagen fibers, opposite to the LOX which is very present with the collagen fibers and little present on the microfibrils. The LOXL antigens were detected in association with the microfibrils and around the elastic fibers of the skin of human foreskin. LOXL is not associated with the amorphous elastin which extends around the microfibrils, but is mainly observed on their periphery, and not with the collagen fibers.

LOXL is associated with the elastic fibers in the reconstructed skin models and in the skin of the human foreskin.

Example 6

Demonstration of the Relationship Between the Expression of LOXL and Elastogenesis LOXL and LOX are expressed in the dermis of the skin of the foreskin taken from young patients (a few months) still having a high elastin synthesis. LOXL is not however expressed in the dermis of adult skin, of the neck, the breast, the abdomen or the face, whereas LOX is always expressed, in the dermis (FIG. 6).

Figure 6:
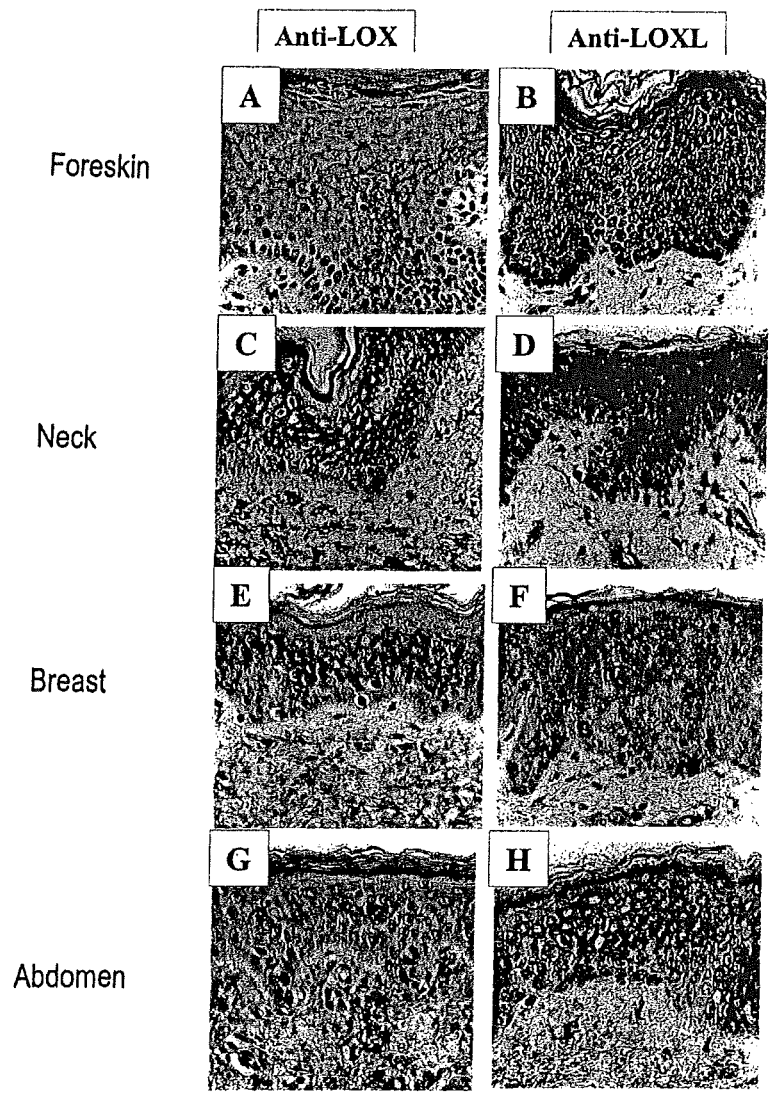

On FIG. 6: the immuno-detection of LOX and LOXL in the human skin is represented.

The antibodies anti-LOX (A, C, E, G) and anti-LOXL (B, D, F, H) were used for detecting the expression of LOX and LOXL in samples of skin of the foreskin (A, B), of the neck (C, D), of the breast (E, F) and of the abdomen (G, H) originating from the tissue bank of the Edouard Herriot Hospital, Lyons, France. The tissues were fixed with Bouin's reagent, included in paraffin, and treated for the immuno-detection as was carried out for the immuno-detections which are described above.

Figure 7:
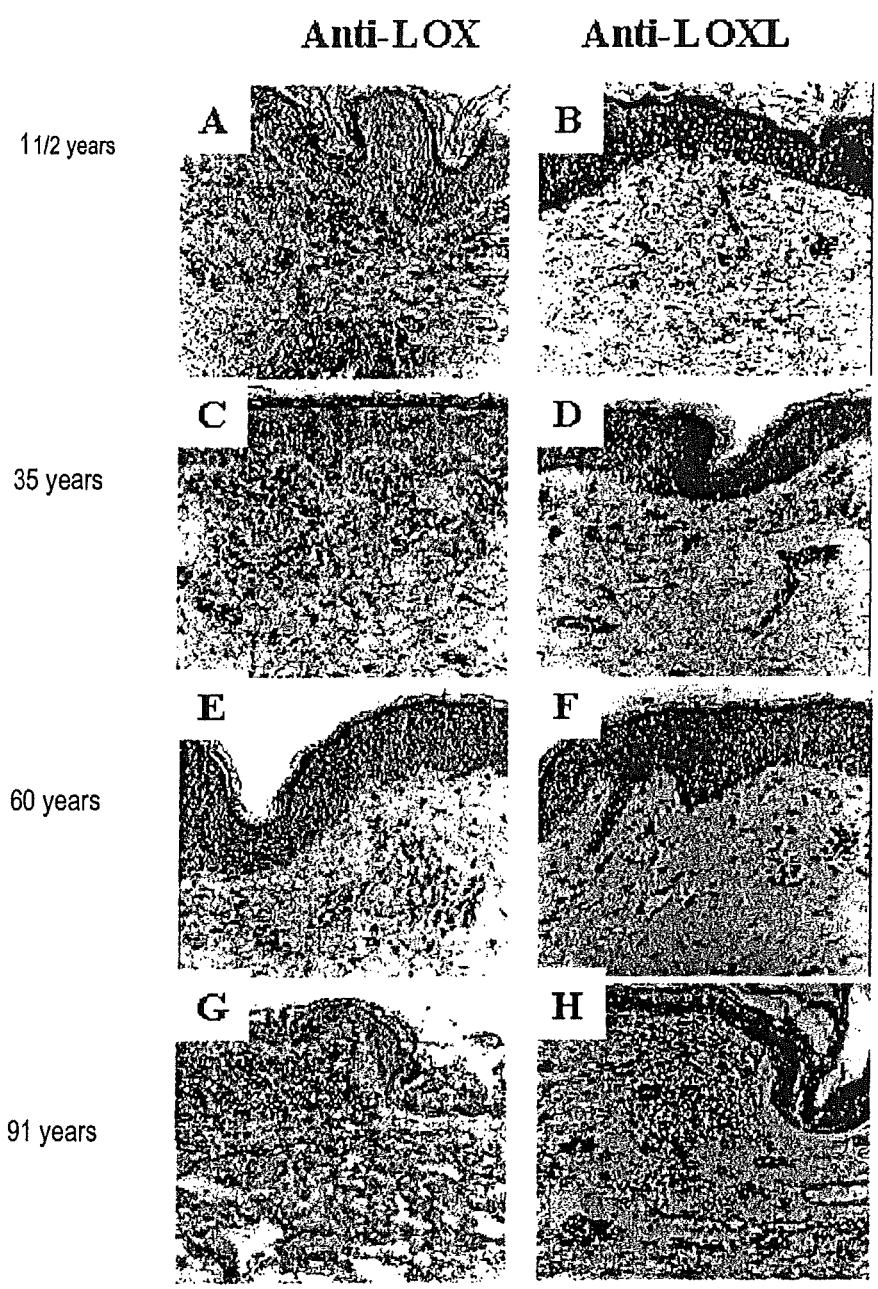

The absence of detection of LOXL in the dermis of the skin of the neck, of the breast, of the abdomen or of the face, is confirmed in the infant and the adult (FIG. 7: abdomen).

On FIG. 7: The immuno-detection of LOX and LOXL in skins of the human abdomen taken at various ages is represented.

The antibodies anti-LOX (A, C, E, G) and anti-LOXL (B, D, F, H) were used for detecting the expression of LOX and LOXL in samples of skin of the abdomen taken at 1.5 years old (A, B), 35 years old (C, D), 60 years old (E, F) and 91 years old (G, H) originating from the tissue bank of the Edouard Herriot Hospital. The tissues were fixed with Bouin's reagent, included in paraffin, and treated for the immuno-detection such as described for the preceding immuno-detections.

During the same pieces of work, a high expression was observed of LOX and LOXL in the epidermis of human skin, with a very late extinction of the expression of these 2 enzymes (91 years old) (FIG. 7).

In the scars, neither LOXL nor LOX were able to be observed in the scar tissue zones 3 months after the scar and 5 years after the scar. It is to be noted that the elastin was immuno-detected at 3 months and disappeared at 5 years in this scar (FIG. 8).

Figure 8:
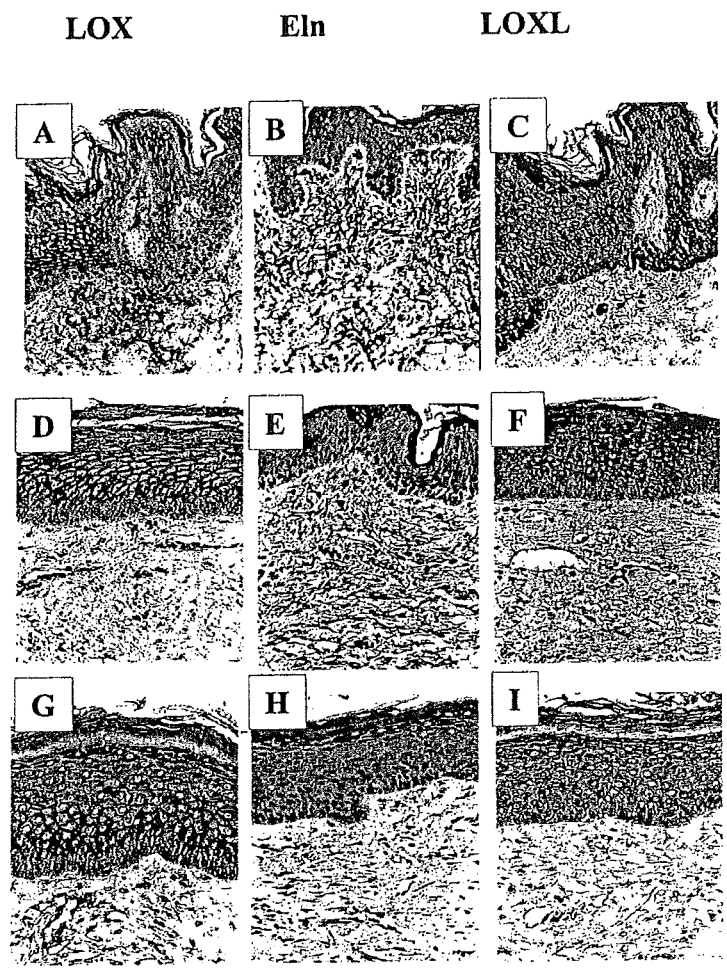

On FIG. 8: The immuno-detection of LOX and LOXL in scar tissue skins at varying periods after the healing is represented.

The antibodies anti-LOX (A, D, G), anti-elastin (B, E, H) and anti-LOXL (C, F, I) were used for detecting the expression of LOX, of elastin and of LOXL in samples of skin of the neck of a patient of 17 years old, around the scar («normal», zone, A-C), 3 months (D-F) or 5 years old (G-H) after a healing. The tissues were fixed with Bouin's reagent, included in paraffin, and treated for the immuno-detection such as was described for the preceding immuno-detections. The labeling of elastin requires a demasking with the aid of 0.2% hyaluronidase (Sigma).

By virtue of these Examples, the invention demonstrates that there exists: (i) an undeniable implication of LOXL in the formation of elastic fibers in reconstructed skin models and in the dermis of the foreskins of young patients, and (ii) a veritable deficit of expression of LOXL in the dermis of the human skin at varying ages and in the scars. LOXL is therefore indeed the only lysyl oxidase isoform which is capable on the one hand of enabling the cross-linking of the functional elastic fibers and, on the other, of being missing in the situation wherein a cross-linking of the elastic fibers is necessary in order to produce functional fibers. LOX, which could also be associated with the formation of elastic fibers, is not missing in the skins of the adult.

Example 7

Study of the Pre-Transcriptional Regulation of the LOXL Gene

Figure 9:
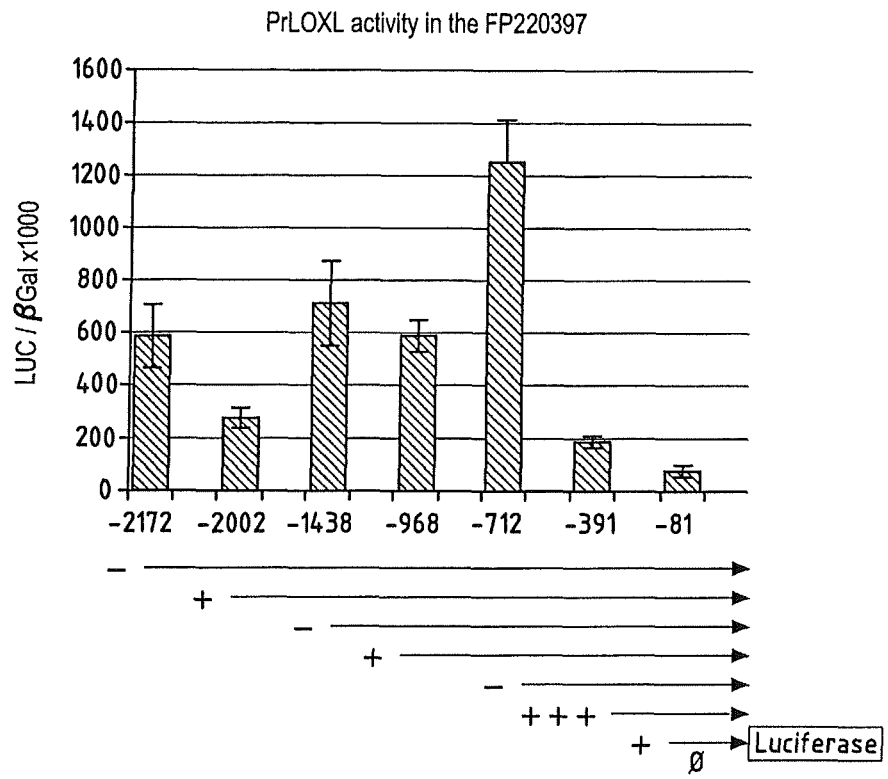

The invention has enabled demonstrating further that the human LOXL gene (hLOXL) can be activated at its promoter level (FIG. 9). The Sequence ID No. 3 describes the nucleotides going from −2730 to −1 of the sequence of this promoter. Several zones of activity of the hLOXL promoter were demonstrated. Notably, the region corresponding to the nucleotides −712/−391 (according to the numbering defined from +1 of translation of the LOXL gene) possesses an up-regulating activity on the reporter gene luciferase, expressed after transitional transfection in fibroblasts of skin of the human foreskin (FIG. 9).

It is therefore a pre-transcriptional up-regulation of the hLOXL gene, which indicates that it is possible to activate the synthesis of this gene, and therefore of the corresponding hLOXL protein, since the inventors had demonstrated beforehand that the variations of the expression of hLOXL can be traced concomitantly at the level of the genes and/or the proteins. This had also been demonstrated for LOX (Decitre et al., Lab. Invest., 78, 143-151, 1998).

A study of the nuclear sequence PrLOXL with the aid of the software Transfac® on the Internet has enabled us to define putative sites of regulation by nuclear factors. These factors were correlated with cytokines or other effectors known for acting on the transcription of certain genes via these transcription factors. The most interesting sites are presented in FIG. 10. This scheme recapitulates this analysis and indicates 2 putative sites of response to retinoic acid, 2 to TGF-β, 1 to EGF, 3 to oestrogens and 2 to glucocorticoids. We have thus been able to define several sites which could regulate the transcription of the LOXL gene, since they were studied in the regulating zones. These are the putative elements of response to retinoic acid, to TGF-β, to EGF and to glucocorticoids. The zones which correspond to these putative sites of regulation by retinoic acid and oestrogens seem to have a real activating effect on the transcription, since the activity of the promoter drops by about 50% and 60% respectively without these elements. The site of regulation by the TGF-β seems to lower the promoting activity.

The tools thus described can be used for the screening of active principles having an agonist or antagonist action upon the promoter of hLOXL, and more particularly upon the putative sites of recognition.

It is so that is advantageous to seek active principles comprising a region which hybridizes with at least one part of the sequence of nucleotides of the promoter of hLOXL, or which induces effector proteins having this property.

Functional Analysis of the Promotor of the hLOXL Gene

The promoter of the human LOXL gene (PrhLOXL) was defined by virtue of the sequences from the data bases. Since the site of initiation of the transcription was unknown, the inventors numbered it with respect to the +1 of translation. However, the EST (Expressed Sequence Tags) cDNA search, which corresponds to this region, did not give any sequence further up from position −342, which enables supposing that the initiation of the transcription of the hLOXL gene is done in this region (without TATA box). Specific primers were shown on this sequence in position −2172 and +189 (exon 1). They enabled the amplification and the isolation of the PrhLOXL from human genomic DNA originating froth skin fibroblasts. It was cloned and sequenced, its sequence proving to be conform to that predicted. Then, the promoter, known as «entire», going from −2172 to −1, was able to be sub-cloned in the pGL3-basic vector (Promega, Charbonnières, France) for the study of it in eukaryotic cells. It was placed up from the reporter gene, the luciferase gene. Thus, the production of luciferase by the transfected cells is under the control of the PrhLOXL and therefore proportional to its activity. The cells are transfected at the same time with the promoter, intensely and reproducibly expressing β-galactosidase (β-Gal), enabling the results to be normalized. For a same condition, the luciferase and β-Gal enzyme activities are measured.

The PrhLOXL was progressively reduced (deletion 5') so as to determine the role of the regions taken out. The aim was to study the regulation of the PrhLOXL in the fibroblasts of human skin, the transfection of these cells was developed. In contrast to the cell lines which transfect easily, normal fibroblasts transfect very poorly. Superfect® (Qiagen, Courtaboeuf, France) was selected, since it enables the transfection of about 40% of fibroblasts in culture.

The constructions made, as well as theft activity in the foreskin fibroblasts, are presented in FIG. 9. The inventors located three large activating regions of the transcription and two inhibiting regions. For example, the region −712→−391 is very activating since the activity of the promoter drops considerably when it is taken out (construction −391→−1).

This study has enabled specifying the zones to be studied for stimulating the transcription of the PrhLOXL.

Notably, FIG. 9 represents the luciferase/β-galactosidase activity as a function of the sequence of the promoter PrhLOXL. This Figure enables facilitating the understanding of the definition of the activating and inhibiting regions of the promoter within a human fibroblast cell of the skin of the foreskin.

The successive reductions of the PrhLOXL in 5' have enabled generating 7 constructions, bearing shorter and shorter sequences of the promoter up, from the reporter gene luciferase pLL-2172, pLL-2002, pLL-1438, pLL-712, –pLL-391, –pLL-81. The constructions were transfected in fibroblasts of the foreskin of human skin, and the luciferase activity was measured. In parallel, the cells are also transfected with a plasmid bearing the β-galactosidase gene, under the control of the promoter SV40, so as to serve as a transfection effectiveness control. The final values correspond to the luciferase activity (indicating the activity of the sequences of the hLOXL promoter) compared to the β-galactosidase activity (showing the effectiveness of transfection). The evolution of the activities enable defining several regulation zones on the promoter, including 3 activating zones, shown by the signs +(−2172→−2002; −1438→−968; −712→−391) and 2 inhibiting zones, shown by the signs. (−2002→−1438; −968→−712). The −81→−1 promoter is not active and is situated down from the +1 of transcription. The putative +1 of transcription is situated in position −342 with respect to the site of initiation of the translation.

Figure 10:
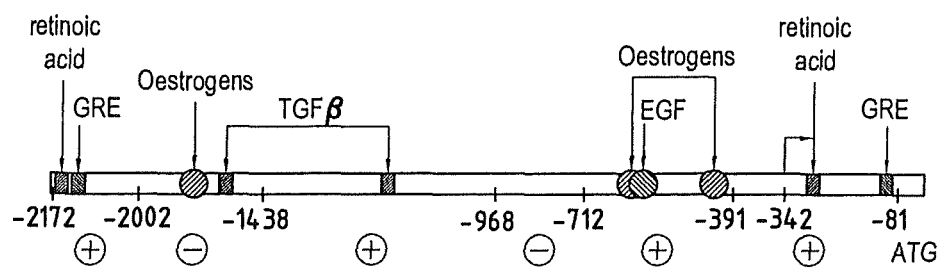

FIG. 10 represents a schematic view of the promoter of the hLOXL gene, and notably identifies the putative sites of regulation of the transcription of the hLOXL gene. The zones indicated by a "+" sign correspond to a zone of activation of the expression of the gene, those represented by a "−" correspond to a zone of inhibition of this expression.

Example 8

Figure 11:

Demonstration of the Activation of LOXL by the Introduction of Keratinocytes in a Reconstructed Skin Model The detection of the expression of the gene encoding LOXL is demonstrated by the in situ hybridization of the messenger RNA of LOXL with double strand DNA probes which are labeled with digoxigenin, on sections included in paraffin.
In FIG. 11, which represents skin model sections (Mimeskin®) at day 35:
(A) the expression of LOXL is positive in the deep dermis and throughout all the epidermis.
(B) The expression of LOX is positive in all the dermis and in the suprabasal layers of the epidermis.
(C) The expression of tropoelastin (TE) is found in association with the dermal fibroblasts and in the epidermis.
(D) The expression of the gene COL1A1 (collagen α1 (I)) is detected in the dermis but not in the epidermis.
(E) Control without probe.
The position of the DEJ is indicated by an open arrow, the position of the porous dermal substrate is indicated with arrows, and the positive cells are indicated with arrow heads.

The double strand DNA probes are produced by PCR. The following primers were used, respectively:
For the gene of the Ialpha1 collagen, sense 5'-GTGGAGAG-TACTGGATTG-3' (SEQ ID No 14) and antisense 5'-TCGT-GCAGCCATCGACAG-3' (SEQ ID No 15), for tropoelastin, sense 5'-GTATATACCCAGGTGGCGTG-3' (SEQ ID No 10) and antisense 5'-CGAACTTTGCTGCTGCTTTTAG-3' (SEQ ID No 11); for hLOX, sense 5'-GGTGGCCGAC-CCCTACTACATCC-3' (SEQ ID No 12) and antisense 5'-GCAAATCGCCTCTGGTAGCCATAGTC-3' (SEQ ID No 13); for hLOXL, sense 5'-GACATAACCGACGTG-CAGCC-3' (SEQ ID No 8) and antisense 5'-ATC-CACGTTTCGCTCCCTGAG-3' (SEQ ID No 9).

The DNAs are amplified with Taq Polymerase (Promega, Charbonnières, France) and Dig-11-dUTP (Roche Diagnostic, Meylan, France) as labeller nucleotide, and they are then purified after electrophoresis on agarose gel by using the QIAquick extraction kit (Qiagen; Courtaboeuf, France). The in situ hybridization was carried out on sections included in paraffin. The samples are ridded of paraffin and treated with proteinase K (Roche) at 2 µg/ml for 15 minutes at 20° C. The endogenous peroxidases are inhibited as indicated in the TSA⁺ amplification kit (NEN, Boston, USA). A pre-hybridization is carried out for 2 hours at 37° C. in 20 mM phosphate buffer at pH 7.4, with 50% deionised formamide, 2×SSC (sodium salt citrate), 5 mM EDTA, 2.5×Denhardt's solution, 200 µg/ml denatured herring DNA, 1 mg/ml salmon sperm DNA, and 10 mg/ml tRNA. The hybridization is carried out for 16 hours at 37° C. in 20 mM phosphate buffer, with 50% deionised formamide, 2×SSC, 5 mM EDTA, 2.5×Denhardt's solution, 200 µg/ml denatured herring sperm DNA, and 10% dextran sulphate, with or without the prior-denatured probe for 5 minutes in a boiling water bath. After the hybridization, the sections are washed at 20° C. (or 37° C. for the collagen) in 2×SSC/50% formamide, 1×SSC/50% formamide, 1×SSC, and 0.5×SSC: After dehydration, the hybrids labelled with the digoxigenin are detected with an anti-DIG antibody conjugated with horseradish peroxidase (Roche). The final detection of the complexes is carried out by using the TSA⁺ amplification kit (NEN). The positive signals correspond to the activity of the alkaline phosphatase linked to the amplification procedure of the TSA kit, after 2 hours of activity at ambient temperature; and defined by the precipitation of the tetrazolium salts formed (by using the Nitro Blue Tetrazolium/bromochlorylindolophosphate (NBT/BCIP) substrates).

The invention demonstrates that the LOXL and LOX genes can be activated by the addition of keratinocytes in a reconstructed skin model (Mimeskin®), Coletica, Lyons, France), as the tracking of the expression of the mRNAs by in situ hybridization demonstrates (FIG. 11).

The induction of the synthesis of LOXL is concomitant with that of tropoelastin (6 days after the addition of keratinocytes on the equivalent dermis).

The LOX gene is also activated after the addition of the keratinocytes, at the same time as the collagen Iα1 gene (Col1A1).

Example 9

Demonstration of a Drop in the Level of the Expression of the LOX Gene in Adult Fibroblasts The inventors used five strains of fibroblasts from the foreskin (FF) (originating from young infants) and 6 strains of adult fibroblasts (AF, 3 of 20 years old on average, and 3 of 60 years old on average) originating from plastic surgery on the abdomen. The expression of the three genes of interest, as well as of actin, was analyzed by real time RT-PCR (quantitative reverse transcriptase polymerase chain reaction; FIG. 12). This technique enables precisely quantifying the expression of a gene in comparing it to that of the actin (considered as constant). The regulation of the level of expression of this gene can therefore be quantified.

The results presented in FIG. 12 first of all show that the synthesis of LOXL mRNA drops spectacularly and statistically significantly in the fibroblasts of adults, and this as from the age of 20 years, with a drop of near to 70% with respect to the fibroblasts of the foreskin, whereas the elastin mRNA does not vary significantly with age. This piece of data is in accordance with the literature on elastin: if the elastic tissue deteriorates and is not replaced, it does not seem to be due to an inhibition of the activity of the elastin gene.

The synthesis of LOX mRNA decreases on average by 40% in the AFs with respect to the FFs, but with the individual variability, this deviation is not very significant.

The total RNAs are purified with the «SV 96Total RNA Isolation System» kit (Promega, Charbonnières, France). The purified RNAs are eluted in 100 µl of RNase-free water (Promega, Charbonnières, France), determined and distributed into plates (96-well, 10 µl total RNA at 5 ng/µl by PCR). The primers selected for the Implementation of this work are the following and are the subject of Table I:

The Examples above demonstrate that the synthesis of the products of the genes LOXL and LOX can be activated at gene level. The activation of the synthesis of the mRNAs of LOXL and of tropoelastin is concomitant in reconstructed skin. The activation of the genes of LOXL and of tropoelastin enables the formation of the elastic fibers. A screening of active principles enables leading to the identification of molecules which can simultaneously re-induce the expression of the genes of elastin and of LOXL, so as to stimulate the elastogenesis.

In conclusion, the invention enables demonstrating the direct relationship of LOXL with the elastic fibers, the importance of LOXL for forming elastic fibers in reconstructed skin, and the absence of LOXL from tissues wherein the synthesis of functional elastic fibers does not take place (adult tissues, scars). The invention relates notably to a method of screening for detecting novel molecules which are capable of concomitantly inducing the synthesis of LOXL and of elastin with the view to re-inducing the expression of functional elastic fibers in reconstructed skin, skin biopsies, and human skin.

TABLE I

| Gene | Name | Size (nucleotides) | Human sequence | Position on the human gene | Melting temperature (MT) |
|---|---|---|---|---|---|
| ELN | 1 Ela | 20 | GTA TAT ACC CAG GTG GCG TG | Sense: +443 | 62° C. |
|  | 2 Ela | 21 | CGA ACT TTG CTG CTG CTT TAG | Antisense: +799 | 62° C. |
| LOX | Ox 64 | 21 | ACG TAC GTG CAG AAG ATG TCC | Sense: +676 | 60° C. |
|  | Ox 65 | 21 | GGC TGG GTA AGA AAT CTG ATG | Antisense: +841 | 59° C. |
| LOXL | 30 L1 | 19 | GAC TTC GGC AAC CTC AAC C | Sense: +1480 | 60° C. |
|  | 30 L2 | 20 | TGT TGC AGA AAC GTA GCG AC | Antisense: +1701 | 60° C. |
| ACTIN | Actin | 20 | GTG GGG CGC CCC AGG CAC CA | U sense | 72° C. |
|  | Actin | 24 | CTC CTT AAT GTC ACG CAC GAT TCC | D antisense | 57° C. |

The technique of real time RT-PCR is carried out with the «Quanti Tect SYBR Green RT-PCR» kit (Qiagen, France) on wells containing mRNA, in an OPTICON thermocycler, which carries out amplification cycles. The retrotranscription (RD is performed for 30 minutes at 50° C., followed by 15 minutes at 95° C. In order to inhibit the reverse transcriptase, to activate the polymerase and to denature the complementary DNA (cDNA) obtained. 50 chain polymerization cycles (PCR) are carried out (15 seconds at 94° C., 30 seconds at 60° C., 30 seconds at 72° C.). At every cycle end, the fluorescence, which is proportional to the number of fragments amplified, is read. The level of expression is defined by the ratio of expression of each gene with respect to actin.

As the preceding pieces of work demonstrate the implication of LOXL in elastogenesis and its disappearance in adults' skins, the following point of the invention has borne upon the levels of expression of the genes LOXL, of LOX and of elastin in fibroblasts of varying ages.

Example 10

Analysis of the Expression of the Messenger RNAs of LOXL and/or of Elastin, e.g. by Qualitative RT-PCR with or without the Placing in Contact of Active Principles the Activity of which is to be Tested The active principles were tested at 1% (v/v) on fibroblasts of normal human skin (originating from the foreskin of the infant or originating from the adult). The culture was carried out, e.g. in a monolayer on 24-well culture plates, in a defined medium without serum (Fibroblast Basal Medium). The cells were sown, e.g. at 40,000 per cm$^2$. At the confluence, the cells are placed in contact with the actives advantageously for 24 hours. In parallel, a non-treated control (medium alone) and three positive controls (TGF-β at 1 ng/ml, IL-1α at 50 pg/ml and Phytokine® (Coletica, Lyons, France) at 2% (v/v)) are advantageously carried out, e.g. on the same culture plate. The TGF-β at 1 ng/ml and the IL-1α at 50 pg/ml were tested beforehand and the stimulation of the synthesis of elastin mRNA induced by these two cytokines at these concentrations was verified by an analysis of the mRNAs, e.g. by quantitative RT-PCR (×10 for TGF-β and ×6 for IL-1 alpha). After the time of placing the actives in contact with the cells, e.g. 24 hours, the media are removed and the cells are preserved e.g. by dry freezing at −80° C. after a rinsing in phosphate buffer pH 7.4. The total RNAs are extracted e.g. with the aid of an extraction kit of 96 wells on silica columns and were determined on a 96-well spectrophotometer at 260 nm (purity indicator: protein determination at 280 nm). The RNAs are diluted e.g. to 5 ng/µl. The qualitative RT-PCR in 1 step is carried out e.g. on 50 ng of initial RNA on a 96-well plate, on the genes of actin, elastin, of LOX and of LOXL. The specific primers of each gene are used e.g. at 0.5 µM:

```
sense elastin gene: 1 Ela
                                    (SEQ ID N° 24)
5'-GTA TAT ACC CAG GTG GCG TG-3';

antisense elastin gene: 2 Ela
                                    (SEQ ID N° 25)
5'-CGA ACT TTG CTG CTG CTT TAG-3';

Sense LOXL gene: 30L1
                                    (SEQ ID N° 26)
5'-GAC TTC GGC AAC CTC AAG C-3';

Antisense LOXL gene: 31L1
                                    (SEQ ID N° 27)
5'-TGT TGC AGA AAC GTA GCG AC-3';

sense LOX gene: 0x64
                                    (SEQ ID N° 28)
5'-ACG TAC GTG CAG AAG ATG TCC-3';

antisense LOX gene: 0x65
                                    (SEQ ID N° 29)
5'-GGC TGG GTA AGA AAT CTG ATG-3';

sense Actin gene: Actin U
                                    (SEQ ID N° 30)
5'-GTGGGGCGCCCCAGGCACCA-3';

antisense Actine gene: Actin
                                    (SEQ ID N° 31)
5'-CTCCTTAATGTCACGCACGATTTC-3'.
```

The amplification parameters were advantageously the following: 48° C., 30 min; 94° C., 2 min; (94° C., 30 seconds; 60° C., 30 seconds; 68° C., 30 seconds) 28 cycles for actin, 30 cycles for LOXL, 32 cycles for LOX, or 34 cycles for elastin; 68° C., 10 min; 14° C., infinity. After amplification, the products are for example mixed at the rate of 3 µl of actin amplification products +5 µl of elastin gene amplification products +5 µl of LOX gene amplification products +5 µl of LOXL gene amplification products. A loading buffer is added (2 µl) and the total volume (20 µl) is deposited on a pre-poured agarose gel (Invitrogen, France) e.g. at 2%. The inventors visualized the levels of expression by means known to the person skilled in the art and e.g.: the bands of the samples were visualized under UV in a black chamber after migration (15 minutes) and were photographed digitally. The photographs of the gels were analyzed by image analysis and quantification of the intensity of the bands (Phoretix1D, France). The level of expression of the genes of elastin, of LOX and of LOXL were expressed in percentage variation with respect to those obtained for the negative control (without treatment).
Interpretations of the Results:
« young » cells and « mature » cells:
It is noted that the cells of the foreskin express quantities of mRNA encoding elastin at a level which is identical to that observed on average in the adult, while they are very much greater than the case of the mRNA encoding LOXL, as well as in the case of the mRNA encoding LOX. It is therefore possible to reverse this decrease of the expression of LOXL and eventually of LOX in the aged cells, and a screening of active principles in this sense was performed.
Screening of Active Principles:

The amounts of cDNA of each test are compared to the amount of actin cDNA and then to the negative controls (without actives). A preliminary analysis enabled considering the tests presenting an increase of elastin (Eln) mRNA of about 1.3 times, of about twice. LOXL, to be significant. Of more than 900 molecules or active extracts tested, 13 actives meet these criteria at the concentrations tested and under the defined conditions. These actives are the following and are the subject of Table II

TABLE II

| Name | Eln Control multiplied by: | LOXL Control multiplied by: | LOX Control multiplied by: |
|---|---|---|---|
| Dill (fruit) | 2.28 | 2.03 | 3.08 |
| currant | 4.11 | 2 | 4.55 |
| Cardamon | 2.08 | 2 | 5.57 |
| Black radish | 2.88 | 2.13 | 2.92 |
| Box holly | 1.58 | 2.4 | 2.53 |
| Cinnamon | 1.56 | 2.09 | 5.08 |
| Lactic ferments | 2.37 | 2.04 | 9.69 |
| Potato | 2.4 | 1.88 | 3.55 |
| Silk protein | 2 | 3.05 | 3.25 |
| Oats | 2.37 | 2.04 | 9.69 |
| *Asa foetida* gum | 1.35 | 2 | 3.19 |
| ethyl hexenoate | 1.5 | 2.33 | 3.09 |
| methyl butyrate | 1.43 | 3.24 | 5.08 |
| ethyl decadienoate | 2.04 | 2.32 | 3.64 |

The plant extracts were obtained in allowing the plants to soak at 2-5% (w/w) in a water/(alcohol, glycol or polyol) mixture (such as ethanol, glycerol, butylene glycol and other glycols, xylitol etc. . . . ) 100/0 to 0/100. The extracts obtained were then filtered or distilled so as to recover the soluble fraction which is then filtered in sterile manner. The chemical molecules originate from Sigma (Saint-Louis, USA) and are used diluted or dispersed at 1% in an alcohol or a glycol.
Conclusion: 13 actives from the bank of 960 actives are capable, under the conditions considered, of significantly activating the level of synthesis of mRNA of the genes encoding LOXL, LOX and elastin, in the fibroblasts of the abdomen of the mature age adult (donor of 63 years old in this case).

Example 11

Study of Effectiveness of a Cosmetic or Dermopharmaceutical Active by e.g. Real Time RT-PCR The actives selected after the first step of screening were tested at various concentrations of between 0.1% and 5%, (v/v) on fibroblasts of normal (adult) human skin. The culture was carried out e.g. in monolayer in 24-well plates, in a defined medium without serum. (Fibroblast Basal Medium). The cells are sown e.g. at 40,000 per cm². After the time of placing the actives in contact with the cells (24 hours), the media were removed and the cells were preserved e.g. by dry freezing at −80° C. after a rinsing with phosphate buffer at pH 7.4. At the end of experimentation, the content of mRNA of elastin, of LOXL and of actin is evaluated by an mRNA analysis technique, e.g. by real time RT-PCR. For this, the couples of primers enabling the amplification of specific fragments of these genes are those described above (Example 10).

After extraction e.g. with the aid of an extraction kit in 96-wells on silica columns and determination on a 96-well spectrophotometer at 260 nm, the RNAs are diluted e.g. to 5 ng/μl. The RT-PCR reactions (Reverse Polymerase Transcription Chain Reactions) were carried out by quantitative real time RT-PCR with the aid of the "Opticon" system (MJ Research). Advantageously, the reaction mixture (50 μl) introduced into the wells was the following, for each sample:

10 μl of RNA at a concentration of 5 ng/μl,
The specific primers of the various labels sought after,
Reaction mixture (Qiagen 25 μl 2xQuantiTect SYBR Green RT-PCR master mix containing 5 mM MgCl2+ 0.5 μl QuantiTect RT mix), the label SYBR Green I inserting in the DNA double strands during the elongation step.

The RT-PCR Conditions were Advantageously the Following:

Reverse Transcription: 30 minutes at 50° C., then 15 minutes at 95° C.,
PCR reactions: [15 seconds at 94° C., 30 seconds at 60° C. and 30 seconds at 72° C.], 50 cycles.

The absence of contamination and the purity of the amplified products were verified e.g. via the fusion curves of the amplified PCR products. The products presenting a double peak or an abnormal fusion temperature were eliminated.

Analysis and Method of Calculation:

The incorporation of fluorescence in the amplified DNA was evaluated continuously during the PCR cycles. This system enabled obtaining curves of fluorescence measurement as a function of the number of PCR cycles and thus enabled evaluating a relative amount of amplified DNA.

In order to take account of the cell population present, all the results were compared to the «actin» signal, which was used as housekeeping gene. According to the experimentation, the threshold of measurement of the C (T) (=Cycle Threshold) was fixed for T between 0.05 and 0.01, and then an arbitrary measurement unit is calculated for each gene according to the formula:

$$S_{gene\,«x»} = 10^7 \times (\tfrac{1}{2})^{C(T)_{gene\,«x»}}$$

$C(T)_{gene\,«x»}$ signifying the number of cycles necessary to attain the cycle threshold of 0.01-0.05 of the gene «x».

The values of the genes of interest were compared to the «actin» signal by calculation of the ratio:

$$R = S_{gene\,«x»}/S_{actin}.$$

These ratios were compared between the treated and non-treated samples, "x" being the LOXL gene, or the elastin gene.

Results: amongst the actives selected, the results obtained, as an example for two of them, are presented in Table III

TABLE III

| Name | LOXL Control multiplied by: | LOX Control multiplied by: | El Control multiplied by: |
|---|---|---|---|
| methyl butyrate at 0.01% | 0.89 | 1.04 | 0.92 |
| methyl butyrate at 0.1% | 1.56 | 1.76* | 0.96 |
| methyl butyrate at 1% | 2.10* | 2.17* | 1.25 |
| methyl butyrate at 5% | 0.91 | 0.91 | 1.70* |
| Silk protein at 0.01% | 1.18 | 0.96 | 1.00 |
| Silk protein at 0.1% | 1.46* | 0.96 | 1.12 |
| Silk protein at 1% | 2.39* | 1.16 | 1.24 |
| Silk protein at 5% | 2.05 | 1.37 | 1.37 |

*statistically significant results p < 0.05 (One Way Anova test)

Conclusion: the actives selected enable activating the level of synthesis of mRNA of the genes encoding LOXL, LOX and elastin, in the fibroblasts of the abdomen of mature age adult (donor of 63 years old in this case): The study made enables determining the optimal concentrations of use for each active selected.

For Examples 1 to 11: the person skilled in the art will know how to draw the adequate teaching from these Examples in order to make variants of the compositions (formulations) described.

Example 12

Use of the Products of the Invention in Cosmetic or Pharmaceutical Formulations of Oil-in-Water Emulsion Type Formulation 12a:

| | | |
|---|---|---|
| A | water | qsp 100 |
| | Butylene Glycol | 2 |
| | Glycerol | 3 |
| | Sodium Dihydroxycetyl Phosphate, Isopropyl Hydroxycetyl Ether | 2 |
| B | Glycol Stearate SE | 14 |
| | Triisononaoin | 5 |
| | Octyl Cocoate | 6 |
| C | Butylene Glycol, Methylparaben, Ethylparaben, Propylparaben, pH adjusted to 5.5 | 2 |
| D | Products of the invention | 0.01-10% |

Formulation 12b:

| | | |
|---|---|---|
| A | Water | qsp 100 |
| | Butylene Glycol | 2 |
| | Glycerol | 3 |
| | Polyacrylamide, Isoparaffin, Laureth-7 | 2.8 |
| B | Butylene Glycol, Methylparaben, Ethylparaben, Propylparaben; | 2 |
| | Phenoxyethanol, Methylparaben, Propylparaben, Butylparaben, Ethylparaben | 2 |
| | Butylene Glycol | 0.5 |
| D | Products of the invention | 0.01-10% |

Formulation 12c:

| | | |
|---|---|---|
| A | Carbomer | 0.50 |
| | Propylene Glycol | 3 |
| | Glycerol | 5 |
| | Water | qsp 100 |
| B | Octyl Cocoate | 5 |
| | Bisabolol | 0.30 |
| | Dimethicone | 0.30 |

| | | |
|---|---|---|
| C | Sodium Hydroxide | 1.60 |
| D | Phenoxyethanol, Methylparaben, Propylparaben, Butylparaben, Ethylparaben | 0.50 |
| E | Perfume | 0.30 |
| F | Products of the invention | 0.01-10% |

Example 13

Use of the Products of the Invention in a Water-in-Oil Type Formulation

| | | |
|---|---|---|
| A | PEG 30 - dipolyhydroxystearate | 3 |
| | Capric Triglycerides | 3 |
| | Cetearyl Octanoate | 4 |
| | Dibutyl Adipate | 3 |
| | Grape Seed Oil | 1.5 |
| | Jojoba Oil | 1.5 |
| | Phenoxyethanol, Methylparaben, Propylparaben, Butylparaben, Ethylparaben | 0.5 |
| B | Glycerol | 3 |
| | Butylene Glycol | 3 |
| | Magnesium Sulphate | 0.5 |
| | EDTA | 0.05 |
| | water | qsp 100 |
| C | Cyclomethicone | 1 |
| | Dimethicone | 1 |
| D | Perfume | 0.3 |
| E | Products of the invention | 0.01-10% |

Example 14

Use of the Products of the Invention in a Formulation of Shampoo or Shower Gel Type

| | | |
|---|---|---|
| A | Xantham Gum | 0.8 |
| | Water | qsp 100 |
| B | Butylene Glycol, Methylparaben, Ethylparaben, Propylparaben | 0.5 |
| | Phenoxyethanol, Methylparaben, Propylparaben, Butylparaben, Ethylparaben | 0.5 |
| C | Citric acid | 0.8 |
| D | Sodium Laureth Sulphate | 40.0 |
| E | Product of the invention | 0.01-10% |

Example 15

Use of the Products of the Invention in a Formulation of Lipstick and Other Anhydrous Product Type

| | | |
|---|---|---|
| A | Mineral Wax | 17.0 |
| | Isostearyl Isostearate | 31.5 |
| | Propylene Glycol Dipelargonate | 2.6 |
| | Propylene Glycol Isostearate | 1.7 |
| | PEG 8 Beeswax | 3.0 |
| | Hydrogenated Palm Kernel Oil Glycerides, Hydrogenated Palm Glycerides | 3.4 |
| | Lanolin Oil | 3.4 |
| | Sesame Oil | 1.7 |
| | Cetyl Lactate | 1.7 |
| | Mineral Oil, Lanolin Alcohol | 3.0 |
| B | Castor Oil | qsp 100 |
| | Titanium Dioxide | 3.9 |
| | CI 15850:1 | 0.616 |
| | CI 45410:1 | 0.256 |
| | CI 19140:1 | 0.048 |
| | CI 77491 | 2.048 |
| C | Products of the invention | 0.01-5% |

Example 16

Use of the Products of the Invention in a Formulation of Aqueous Gels (Eyeliners, Slimmers, etc.)

| | | |
|---|---|---|
| A | water | qsp 100 |
| | Carbomer | 0.5 |
| | Butylene Glycol | 15 |
| | Phenoxyethanol, Methylparaben, Propylparaben, Butylparaben, Ethylparaben | 0.5 |
| B | Products of the invention | 0.01-10% |

Example 17

Preparation of Pharmaceutical Formulations Containing LOXL

Formulation 17a: Preparation of Tablets

| | | |
|---|---|---|
| A | Excipients | In g, per tablet |
| | Lactose | 0.359 |
| | Sucrose | 0.240 |
| B | Extract of LOXL* | 0.001-0.1 |

*The extract of LOXL is obtained for example according to the method of extraction described in Example 2, followed by a drying step.

Formulation 17b: Preparation of an Ointment

| | | |
|---|---|---|
| A | Excipients | |
| | Low density polyethylene | 5.5 |
| | Liquid paraffin | qsp 100 |
| B | Extract of LOXL* | 0.001-0.1 |

*The extract of LOXL is obtained for example according to the method of extraction described in Example 2, optionally followed by a drying step.

Formulation 17c: Preparation of an Injectable Formula

| | | |
|---|---|---|
| A | Excipient | |
| | Saline isotonic solution | 5 ml |
| B | Extract of LOXL* | 0.001-0.1 g |

*The extract of LOXL is obtained for example according to the method of extraction described in Example 2, followed by a drying step.

Phase A and Phase B are packaged in separate ampoules and are mixed before use.

Example 18

Evaluation of the Cosmetic Acceptance of a Preparation Containing the Subject of the Invention Toxicology tests were carried out on the compounds obtained according to Examples 10 and 11 incorporated at 10% in a 0.5% xanthan gum, by an ocular evaluation, in the rabbit, by the study of the absence of abnormal toxicity by single oral administration in the rat and by the study of the sensitizing power in the guinea pig.

Evaluation of the Primary Irritation of the Skin in the Rabbit:

The preparations described above were applied without dilution at the dose of 0.5 ml on the skin of 3 rabbits according to the method recommended by the OECD in relation to the study of « the acute irritant/corrosive effect on the skin ».

The products are classed according to the criteria defined in the Decision of Feb. 1, 1982 published in the Official Journal of the French Republic (the "JORP") of Feb. 21, 1982.

The results of these tests have enabled concluding that the preparation containing the compound obtained according to Example 11 was classed as non-irritant for the skin.

Evaluation of the Ocular Irritation in the Rabbit

The preparations described above were instilled pure and in one batch at the rate of 0.1 ml in the eye of three rabbits according to the method recommended by the directive of the OECD NO. 405 of Feb. 24, 1987, in relation to the study of "the acute irritant/corrosive effect on the eyes".

The results of this test enable concluding that the preparations can be considered as non-irritant for the eyes, in the sense of the Directive 91/326 EEC, used pure or without dilution.

Test on the Absence of Abnormal Toxicity by Single Oral Administration in the Rat:

The preparations described were administered in one batch orally at the dose of 5 g/Kg of body weight, to 5 male rats and 5 female rats of a protocol inspired from the Directive of the OECD No. 401 of Feb. 24, 1987 and adapted to cosmetic products.

The LD0 and LD50 are found to be greater than 5,000 mg/Kg. The preparations tested are therefore not classed amongst the preparations which are dangerous by ingestion.

Evaluation of the Skin Sensitization Potential in the Guinea Pig

The preparations described are subjected to the maximization test described by Magnusson and Kligmann, a protocol which is in agreement with the directive line No. 406 of the OECD. The preparations are classed as non-sensitizing by contact with the skin.

Precisions on the sequences which are described:

Sequence ID No 1: is the peptide sequence of the human protein LOXL.

Sequence ID No 2: is the sequence of nucleotides of the cDNA encoding the human protein LOXL described in sequence ID No 1.

Sequence ID No 3: is the sequence of nucleotides of the cDNA encoding the promoter of the human gene encoding the protein LOXL described in sequence ID No 1.

Sequence ID No 4: is the peptide sequence of the human protein tropoelastin.

Sequence ID No 5: is the sequence of nucleotides of the cDNA encoding the human protein tropoelastin described in sequence ID No 4.

Sequence ID No 6: is the peptide sequence of the human protein LOX.

Sequence ID No 7: is the sequence of nucleotides of the cDNA encoding the human protein LOX described in sequence ID No 6.

For the double strand DNA probes:

Sequence ID No 8: is a sense primer of the DNA encoding the human protein LOXL described in sequence ID No 1

Sequence ID No 9: is an antisense primer of the DNA encoding the human protein LOXL described in sequence ID No 1.

Sequence ID No 10: is a sense primer of the DNA encoding the human protein tropoelastin described in sequence ID No 4.

Sequence ID No 11: is an antisense primer of the DNA encoding the human protein tropoelastin described in sequence ID No 4.

Sequence ID No 12: is a sense primer of the DNA encoding the human protein LOX described in sequence ID No 6.

Sequence ID No 13: is an antisense primer of the DNA encoding the human protein LOX described in sequence ID No 6.

Sequence ID No 14: is a sense primer of the DNA encoding the human protein collagen I α1L.

Sequence ID No 15: is an antisense primer of the DNA encoding the human protein collagen I α1L.

For the fusion genes GST:

Sequence ID No 16 is a sense primer of the DNA of the fusion gene GST S355-D415.

Sequence ID No 17: is an antisense primer of the DNA of the fusion gene GST S355-D415.

Sequence ID No 18: is a sense primer of the DNA of the fusion gene GST G128-L212.

Sequence ID No 19: is an antisense primer of the DNA of the fusion gene GST G128-L212.

Sequence ID No 20: is a sense primer of the DNA of the fusion gene GST V228-S279.

Sequence ID No 21: is an antisense primer of the DNA of the fusion gene GST V228-S279.

Sequence ID No 22: is a sense primer of the DNA of the fusion gene GST D306-N373.

Sequence ID No 23: is an antisense primer of the DNA of the fusion gene GST D306-N373.

For the PCR primers:

Sequence ID No 24: is a sense primer for the RT-PCR of the mRNA encoding the human protein tropoelastin described in sequence ID No 4.

Sequence ID No 25: is an antisense primer for the RT-PCR of the mRNA encoding the human protein tropoelastin described in sequence ID No 4.

Sequence ID No 26: is a sense primer for the RT-PCR of the mRNA encoding the human protein LOXL described in sequence ID No 1.

Sequence ID No 27: is an antisense primer of the sequence of the mRNA encoding the human protein LOXL described in sequence ID No 1.

Sequence ID No 28: is a sense primer for the RT-PCR of the mRNA encoding the human protein LOX described in sequence ID No 6.

Sequence ID No 29: is an antisense primer for the RT-PCR of the mRNA encoding the human protein LOX described in sequence ID No 6.

Sequence ID No 30: is a sense primer for the RT-PCR of the mRNA encoding the human protein actin.

Sequence ID No 31: is an antisense primer for the RT-PCR of the mRNA encoding the human protein actin.

What is claimed is:

1. A cosmetic method of skin care in a human in need of stimulating formation of elastic fibers in the skin of the human, comprising applying a substance selected from the group consisting of an extract of dill fruits obtained by soaking the dill fruits in water or in water/(alcohol, glycol or polyol) mixture, an extract of cardamon, an extract of currant, an extract of black radish, and ethyl decadienoate onto skin of the human in need thereof in an amount effective to obtain a stimulated formation of elastic fibers effect in the skin of the human in need thereof, wherein said substance stimulates formation of elastic fibers in the skin compared to a control application without said substance and wherein the skin of the human in need thereof is normal skin.

2. The method of claim 1, wherein the substance stimulates enzymatic activity or increases expression of the L isoform of lysyl oxidase (LOXL).

3. The method of claim 2, wherein the substance increases expression of the LOXL by increasing expression of a nucleic acid encoding the LOXL or by increasing expression of a polypeptide comprising a fraction of the LOXL.

4. The method of claim 3, wherein the LOXL comprises the amino acid sequence of SEQ ID NO: 1 or is encoded by a nucleic acid comprising the nucleotide sequence of SEQ ID NO: 2.

5. The method of claim 2, wherein the LOXL stimulates expression of the protein elastin.

6. The method of claim 1, wherein the substance is applied onto the skin of the human in need thereof with a cosmetically acceptable excipient in a cosmetic composition.

7. The method of claim 6, wherein the substance is at a concentration between 0.01% and 10% (v/v) of the cosmetic composition.

8. The method of claim 6, wherein the substance is at a concentration between 0.1% and 5% (v/v) of the cosmetic composition.

9. The method of claim 6, wherein the cosmetic composition further comprises a second substance that stimulates expression of elastin.

10. The method of claim 9, wherein the second substance also stimulates enzymatic activity or increases expression of the LOXL.

11. The method of claim 1 wherein the substance is ethyl decadienoate.

12. The method of claim 3, wherein the substance is ethyl decadienoate.

13. The method of claim 6, wherein the substance is ethyl decadienoate.

14. The method of claim 1, wherein the substance is an extract of dill fruits obtained by soaking the dill fruits in water or in water/(alcohol, glycol or polyol) mixture.

15. The method of claim 1, wherein the stimulated formation of elastic fibers in the skin of the human in need thereof provides at least one cosmetic benefit to the skin selected from the group consisting of for combating against loosening of tissues, for densifying extracellular matrix, for firming up subcutaneous tissues, for reducing skin wrinkles, for improving appearance and quality of scar tissue, for improving appearance and quality of dystrophic, for improving appearance and quality of keloid scars, and for combating against stretch marks.

16. The method of claim 1, wherein the at least one cosmetic benefit is for combating against loosening of tissues during ageing or during solar exposures.

17. The method of claim 16, wherein the substance increases expression of the LOXL by increasing expression of a nucleic acid encoding the LOXL or by increasing expression of a polypeptide comprising a fraction of the LOXL.

18. The method of claim 17, wherein the substance is an extract of dill fruits obtained by soaking the dill fruits in water or in water /(alcohol, glycol or polyol) mixture or ethyl decadienoate, or a mixture thereof.

19. The method of claim 1, wherein the stimulated formation of elastic fibers in the skin of the human in need thereof provides an anti-wrinkle or anti-ageing effect on the skin.

20. The method of claim 1, wherein the extract of dill fruit is obtained by soaking the dill fruits in water.

* * * * *

SEQUENCE LISTING

<160> NUMBER OF SEQ ID NOS: 31

<210> SEQ ID NO 1
<211> LENGTH: 574
<212> TYPE: PRT
<213> ORGANISM: Homo sapiens

<400> SEQUENCE: 1

```
Met Ala Leu Ala Arg Gly Ser Arg Gln Leu Gly Ala Leu Val Trp Gly
 1               5                  10                  15

Ala Cys Leu Cys Val Leu Val His Gly Gln Gln Ala Gln Pro Gly Gln
            20                  25                  30

Gly Ser Asp Pro Ala Arg Trp Arg Gln Leu Ile Gln Trp Glu Asn Asn
        35                  40                  45

Gly Gln Val Tyr Ser Leu Leu Asn Ser Gly Ser Glu Tyr Val Pro Ala
    50                  55                  60

Gly Pro Gln Arg Ser Glu Ser Ser Arg Val Leu Leu Ala Gly Ala
65                  70                  75                  80

Pro Gln Ala Gln Gln Arg Arg Ser His Gly Ser Pro Arg Arg Gln
                85                  90                  95

Ala Pro Ser Leu Pro Leu Pro Gly Arg Val Gly Ser Asp Thr Val Arg
            100                 105                 110

Gly Gln Ala Arg His Pro Phe Gly Phe Gly Gln Val Pro Asp Asn Trp
        115                 120                 125

Arg Glu Val Ala Val Gly Asp Ser Thr Gly Met Ala Leu Ala Arg Thr
    130                 135                 140

Ser Val Ser Gln Gln Arg His Gly Gly Ser Ala Ser Ser Val Ser Ala
145                 150                 155                 160

Ser Ala Phe Ala Ser Thr Tyr Arg Gln Gln Pro Ser Tyr Pro Gln Gln
                165                 170                 175

Phe Pro Tyr Pro Gln Ala Pro Phe Val Ser Gln Tyr Glu Asn Tyr Asp
            180                 185                 190

Pro Ala Ser Arg Thr Tyr Asp Gln Gly Phe Val Tyr Arg Pro Ala
            195                 200                 205

Gly Gly Gly Val Gly Ala Gly Ala Ala Val Ala Ser Ala Gly Val
        210                 215                 220

Ile Tyr Pro Tyr Gln Pro Arg Ala Arg Tyr Glu Tyr Gly Gly Gly
225                 230                 235                 240

Glu Glu Leu Pro Glu Tyr Pro Pro Gln Gly Phe Tyr Pro Ala Pro Glu
                245                 250                 255

Arg Pro Tyr Val Pro Pro Pro Pro Pro Asp Gly Leu Asp Arg
            260                 265                 270

Arg Tyr Ser His Ser Leu Tyr Ser Glu Gly Thr Pro Gly Phe Glu Gln
    275                 280                 285

Ala Tyr Pro Asp Pro Gly Pro Glu Ala Ala Gln Ala His Gly Gly Asp
    290                 295                 300

Pro Arg Leu Gly Trp Tyr Pro Tyr Ala Asn Pro Pro Glu Ala
305                 310                 315                 320

Tyr Gly Pro Pro Arg Ala Leu Glu Pro Pro Tyr Leu Pro Val Arg Ser
                325                 330                 335

Ser Asp Thr Pro Pro Gly Gly Glu Arg Asn Gly Ala Gln Gln Gly
            340                 345                 350

Arg Leu Ser Val Gly Ser Val Tyr Arg Pro Asn Gln Asn Gly Arg Gly
        355                 360                 365
```

```
Leu Pro Asp Leu Val Pro Asp Pro Asn Tyr Val Gln Ala Ser Thr Tyr
    370                 375                 380

Val Gln Arg Ala His Leu Tyr Ser Leu Arg Cys Ala Ala Glu Glu Lys
385                 390                 395                 400

Cys Leu Ala Ser Thr Ala Tyr Ala Pro Glu Ala Thr Asp Tyr Asp Val
                405                 410                 415

Arg Val Leu Leu Arg Phe Pro Gln Arg Val Lys Asn Gln Gly Thr Ala
                420                 425                 430

Asp Phe Leu Pro Asn Arg Pro Arg His Thr Trp Glu Trp His Ser Cys
            435                 440                 445

His Gln His Tyr His Ser Met Asp Glu Phe Ser His Tyr Asp Leu Leu
    450                 455                 460

Asp Ala Ala Thr Gly Lys Lys Val Ala Glu Gly His Lys Ala Ser Phe
465                 470                 475                 480

Cys Leu Glu Asp Ser Thr Cys Asp Phe Gly Asn Leu Lys Arg Tyr Ala
                485                 490                 495

Cys Thr Ser His Thr Gln Gly Leu Ser Pro Gly Cys Tyr Asp Thr Tyr
                500                 505                 510

Asn Ala Asp Ile Asp Cys Gln Trp Ile Asp Ile Thr Asp Val Gln Pro
            515                 520                 525

Gly Asn Tyr Ile Leu Lys Val His Val Asn Pro Lys Tyr Ile Val Leu
            530                 535                 540

Glu Ser Asp Phe Thr Asn Asn Val Val Arg Cys Asn Ile His Tyr Thr
545                 550                 555                 560

Gly Arg Tyr Val Ser Ala Thr Asn Cys Lys Ile Val Gln Ser
                565                 570

<210> SEQ ID NO 2
<211> LENGTH: 1725
<212> TYPE: DNA
<213> ORGANISM: Homo sapiens

<400> SEQUENCE: 2
atggctctgg cccgaggcag ccggcagctg ggggccctgg tgtgggcgc  ctgcctgtgc      60 gtgctggtgc acgggcagca ggcgcagccc ggcagggct  cggaccccgc cgctggcgg      120 cagctgatcc agtgggagaa caacgggcag gtgtacagct tgctcaactc gggctcagag     180
tacgtgccgg ccgacctca  gcgctccgag agtagctccc gggtgctgct ggccggcgcg     240
ccccaggccc agcagcggcg cagccacggg agccccggc  gtcggcaggc gccgtccctg     300
cccctgccgg ggcgcgtggg ctcggacacc gtgcgcggcc aggcgcggca cccattcggc     360
tttggccagg tgcccgacaa ctggcgcgag gtggccgtcg ggacagcac  gggcatggcc     420 ctggcccgca cctccgtctc ccagcaacgg cacgggggct ccgcctcctc ggtctcggct     480
tcggccttcg ccagcaccta ccgccagcag ccctcctacc gcagcagtt  ccctaccccg     540 caggcgccct tcgtcagcca gtacgagaac tacgaccccg tcgcggac  ctacgaccag     600 ggtttcgtgt actaccggcc gcgggcggc ggcgtgggcg cggggcggc  ggccgtggcc     660 tcggcggggg tcatctaccc ctaccagccc cgggcgcgct acgaggagta cggcggcggc     720
gaagagctgc ccgagtaccc gcctcagggc ttctacccgg ccccgagag  ccctacgtg      780 ccgccgccgc cgccgccccc cgacggcctg gaccgccgct actcgcacag tctgtacagc     840
gagggcaccc ccggcttcga gcaggcctac cctgaccccg tcccgaggc  ggcgcaggcc     900 catggcggag acccacgcct gggctggtac ccgccctacg ccaacccgcc gcccgaggcg     960
```

```
tacgggccgc cgcgcgcgct ggagccgccc tacctgccgg tgcgcagctc cgacacgccc    1020
ccgccgggtg gggagcggaa cggcgcgcag cagggccgcc tcagcgtagg cagcgtgtac    1080
cggcccaacc agaacggccg cggtctccct gacttggtcc cagaccccaa ctatgtgcaa    1140
gcatccactt atgtgcagag agcccacctg tactccctgc gctgtgctgc ggaggagaag    1200
tgtctggcca gcacagccta tgcccctgag gccaccgact acgatgtgcg ggtgctactg    1260
cgcttccccc agcgcgtgaa gaaccagggc acagcagact ccctcccccaa ccggccacgg   1320 cacacctggg agtggcacag ctgccaccag cattaccaca gcatggacga gttcagccac    1380
tacgacctac tggatgcagc cacaggcaag aaggtggccg agggccacaa ggccagtttc    1440
tgcctggagg acagcacctg tgacttcggc aacctcaagc gctatgcatg cacctctcat    1500
acccagggcc tgagcccagg ctgctatgac acctacaatg cggacatcga ctgccagtgg    1560
atcgacataa ccgacgtgca gcctgggaac tacatcctca aggtgcacgt gaacccaaag    1620
tatattgttt tggagtctga cttcaccaac aacgtggtga gatgcaacat tcactacaca    1680
ggtcgctacg tttctgcaac aaactgcaaa attgtccaat cctga                    1725

<210> SEQ ID NO 3
<211> LENGTH: 2731
<212> TYPE: DNA
<213> ORGANISM: Homo sapiens

<400> SEQUENCE: 3
gtggaagtgg gggccacccc caagagataa ccccctcctt tctctcacaa gtcaagagaa     60
agaagaaaat agtggccaca tgtctggctc tgtgctgggg actttttcata atcctctcat   120 tccatcctct caaatatgcc acaagaaagg tatgattacc cccaggtcac agacgggact    180
ctgaagctct gagagcttaa aaagcttccc cggggagtgg ctgggccagg ccaggtccct    240
agctcaagtc atggtgtgga ccccaggtc tccatctcag cagggatggc tggcaggagc     300
gcagtcctgg ccaggggagt ctgtgcagag gcccaggcta tgttcagagc agagtttatt    360
caaatagagc ctaacaggaa acttggctcc tctgactcac tctgattcga ccttattaag    420
aaaaaaagag agaggagcag gagccagcat cgggtaaggt ttcacgccaa gagctggctc    480
tgaggcccgc tgagtggaat ggcatgtgcc ctgatccccc cacatccaaa gccttgaggc    540
agcccctgcc ctgctgtccg agtcaaggcg aggggtcctg ccttcacgtt agggcaactg    600
agttcccttc ctcacagcca tcctctgtcc tccctccact cctcttccct tccctcccctg   660 cctagggta ccctgaggcc tgtttccatt tctccccctc ctctgctgca gcagctgccc     720
atctggctgg cgggagggcc ctacaggacc ccagggattc caagcagctg aggccaacac    780
tgcagggggc aagcaggagg gagggaaggc ttaaccctcc aggtcccggc cctcagtaag    840
ccctgcctca gcatcttgct tggtgtcagt cacaccagtg gctctttgga ggaatcttgt    900
ctggagtctg agatggaaac ccatgctgg ggagctgagg tgtcagcgtt gacaagttgc     960
tggccaggag gtattggaag cccctacct ctgggctgga ttctgggcat ttaaagggta    1020
gagacatgct ggagtccaag cctcagtcct gaagaacagt gcaatgggtg aacaaatgct   1080
gcctggcaag gatggggttg ggaggtctat agttcccaaa gaatgtccac tctagttgcc   1140
tcctctctag gtgggctcca ggcatttcca aaataaagaa tatacaggag ccaaattaag   1200
gacaggtcct tcataccttg tttataagcc caagagggca atttctgccc ttcggttccc   1260
aggaacacgt tggagaagg cagcccaggg gaggccagaa gagcagtatt tggagtgtga   1320
tttcttggat gccaaagcgt tcaaacttct gggaccccct cctatccctg ccattcccag   1380
```

```
aaggaacaga gaatctccca aagcactctc aggagccatc tggcctaatc ttccattggt    1440
aagctgtggc acctggatca gatagagtaa gggactaagc cacacagcaa caggaccagg    1500
ccaggtctcc ggaacccct tctgttgttc aatgcttact ggcttctctg cctcacagtg    1560 accctgtcc catatcaaag acagccccca gtttcatttt atccatgtgt acactcaagt    1620
tattcccagg ctatgcagag ccaagagatg taggacagaa accatacgtg atgtctggga    1680
agttgatctc tcccaggatc tcacaagtgc ttttcagctc agggatacac cccactcttc    1740
agactgggaa agtaagcccc tgaggtgtgc cacgagggaa aagctgcagc tccagtgcct    1800
ctcttcgcag gcccaagagc tgcggtgcac ctgggacctg gaattagaga gtggtccctg    1860
ttcagcatct ccccgaggag gcccaccaac aaagagggtg tgtctttttt ttttttttct    1920
tcctattgag ggtgtgggat aatggtggaa ggaacatgca aagagggtgt gtcttaatta    1980
gcactggctt tagggaacaa ggaaaaggga aacccggga gtacgggaag gaggctgggg     2040
cagacaggag tcagaggccc attccagccc aaacgagaag ccagtgagca aggtggagac    2100
cagggatgct gtgaccaaag cagagaggaa tgggcggggt ggtgctgaca ccccagcccc    2160
gttctgcctg ccagagcccc acttaccagg cccgagtccc cagaggtccc ctcctactcc    2220
ctgctcgatt cccttcctca gaggcaggtc tgtggcttgg ctgggaactc cagggactga    2280
gggagcactg cagctgtggg accggcgcat agctaaaagc cggcgggcca tagggccccg    2340
cggaggaggc cccagcaggc ggaccaggag gccgaagcct cccgacgctc ccagcctgtt    2400
gcttattcat tcagagtggg aaagcgccag ccgagcggcc agccagtgcg gggctggcca    2460
tgtaaggccc acaggcggtc ctgcccgccc ggtgccctgc ggagagcctc gtgcagccct    2520
gggcaccgcc cctgccctgc cctgaccct tggccttgaa atgctgtcat cggaggagcc     2580
gtcccgctcg ggacaaggcc agcatggaca aagctagagc tggggcaagc aaggagcctt    2640
cctgtcctcg aggccgtggg aagagaagca cgcccaggc cactcctgag agcctctctg     2700
tccaccaggc ctctgcagag gggtcaccat g                                   2731
```

<210> SEQ ID NO 4
<211> LENGTH: 788
<212> TYPE: PRT
<213> ORGANISM: Homo sapiens

<400> SEQUENCE: 4

```
Met Ala Gly Leu Thr Ala Ala Pro Arg Pro Gly Val Leu Leu Leu
1               5                   10                  15

Leu Leu Ser Ile Leu His Pro Ser Arg Pro Gly Val Pro Gly Ala
            20                  25                  30

Ile Pro Gly Gly Val Pro Gly Val Phe Tyr Pro Gly Ala Gly Leu
            35                  40                  45

Gly Ala Leu Gly Gly Gly Ala Leu Gly Pro Gly Gly Lys Pro Leu Lys
        50                  55                      60

Pro Val Pro Gly Gly Leu Ala Gly Ala Gly Leu Ala Gly Leu Gly
65                  70                  75                  80

Ala Phe Pro Ala Val Thr Phe Pro Gly Ala Leu Val Pro Gly Val
                85                  90                  95

Ala Asp Ala Ala Ala Ala Tyr Lys Ala Ala Lys Ala Gly Ala Gly Leu
                    100                 105                 110

Gly Gly Val Pro Gly Val Gly Gly Leu Gly Val Ser Ala Gly Ala Val
                115                 120                 125
```

```
Val Pro Gln Pro Gly Ala Gly Val Lys Pro Gly Lys Val Pro Gly Val
    130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
        195                 200                 205

Lys Ala Pro Lys Leu Pro Gly Gly Tyr Gly Leu Pro Tyr Thr Thr Gly
    210                 215                 220

Lys Leu Pro Tyr Gly Tyr Gly Pro Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Gly
            260                 265                 270

Val Leu Pro Gly Val Gly Gly Ala Gly Val Pro Gly Val Pro Gly Ala
    275                 280                 285

Ile Pro Gly Ile Gly Gly Ile Ala Gly Val Gly Thr Pro Ala Ala Ala
    290                 295                 300

Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
        355                 360                 365

Ser Pro Glu Ala Ala Ala Lys Ala Ala Lys Ala Ala Lys Tyr Gly
    370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415

Val Ala Gly Val Pro Ser Val Gly Gly Val Pro Gly Val Gly Gly Val
            420                 425                 430

Pro Gly Val Gly Ile Ser Pro Glu Ala Gln Ala Ala Ala Ala Lys
        435                 440                 445

Ala Ala Lys Tyr Gly Ala Ala Gly Ala Gly Val Leu Gly Gly Leu Val
    450                 455                 460

Pro Gly Pro Gln Ala Ala Val Pro Gly Val Pro Gly Thr Gly Gly Val
465                 470                 475                 480

Pro Gly Val Gly Thr Pro Ala Ala Ala Ala Lys Ala Ala Lys
                485                 490                 495

Ala Ala Gln Phe Gly Leu Val Pro Gly Val Gly Val Ala Pro Gly Val
            500                 505                 510

Gly Val Ala Pro Gly Val Gly Val Ala Pro Gly Val Gly Leu Ala Pro
        515                 520                 525

Gly Val Gly Val Ala Pro Gly Val Gly Val Ala Pro Gly Val Gly Val
    530                 535                 540

Ala Pro Gly Ile Gly Pro Gly Gly Val Ala Ala Ala Ala Lys Ser Ala
```

```
                 545                 550                 555                 560
    Ala Lys Val Ala Ala Lys Ala Gln Leu Arg Ala Ala Gly Leu Gly
                     565                 570                 575
    Ala Gly Ile Pro Gly Leu Gly Val Gly Val Gly Val Pro Gly Leu Gly
                     580                 585                 590
    Val Gly Ala Gly Val Pro Gly Leu Gly Val Gly Ala Gly Val Pro Gly
                     595                 600                 605
    Phe Gly Ala Val Pro Gly Ala Asp Glu Gly Val Arg Arg Ser Leu Ser
                     610                 615                 620
    Pro Glu Leu Arg Glu Gly Asp Pro Ser Ser Gln His Leu Pro Ser
    625                 630                 635                 640
    Thr Pro Ser Ser Pro Arg Val Pro Gly Ala Leu Ala Ala Lys Ala
                     645                 650                 655
    Ala Lys Tyr Gly Ala Ala Val Pro Gly Val Leu Gly Gly Leu Gly Ala
                     660                 665                 670
    Leu Gly Gly Val Gly Ile Pro Gly Gly Val Val Gly Ala Gly Pro Ala
                     675                 680                 685
    Ala Ala Ala Ala Ala Lys Ala Ala Lys Ala Ala Gln Phe Gly
                     690                 695                 700
    Leu Val Gly Ala Ala Gly Leu Gly Gly Leu Gly Val Gly Gly Leu Gly
    705                 710                 715                 720
    Val Pro Gly Val Gly Gly Leu Gly Gly Ile Pro Pro Ala Ala Ala
                     725                 730                 735
    Lys Ala Ala Lys Tyr Gly Ala Ala Gly Leu Gly Gly Val Leu Gly Gly
                     740                 745                 750
    Ala Gly Gln Phe Pro Leu Gly Gly Val Ala Ala Arg Pro Gly Phe Gly
                     755                 760                 765
    Leu Ser Pro Ile Phe Pro Gly Gly Ala Cys Leu Gly Lys Ala Cys Gly
                     770                 775                 780
    Arg Lys Arg Lys
    785

<210> SEQ ID NO 5
<211> LENGTH: 2367
<212> TYPE: DNA
<213> ORGANISM: Homo sapiens

<400> SEQUENCE: 5
atggcgggtc tgacggcggc ggccccgcgg cccggagtcc tcctgctcct gctgtccatc      60
ctccacccct ctcggcctgg agggtccct ggggccattc tggtggagt tcctggagga     120 gtcttttatc caggggctgg tctcggagcc cttggaggag gagcgctggg gcctggaggc     180
aaacctctta agccagttcc cggagggctt gcgggtgctg gccttggggc agggctcggc     240
gccttccccg cagttacctt tccgggggct ctggtgcctg gtggagtggc tgacgctgct     300
gcagcctata aagctgctaa ggctggcgct gggcttggtg gtgtcccagg agttggtggc     360
ttaggagtgt ctgcaggtgc ggtggttcct cagcctggag ccggagtgaa gcctgggaaa     420
gtgccgggtg tggggctgcc aggtgtatac ccaggtggcg tgctcccagg agctcggttc     480
cccggtgtgg gggtgctccc tggagttccc actggagcag gagttaagcc caaggctcca     540
ggtgtaggtg gagcttttgc tggaatccca ggagttggac cctttggggg accgcaacct     600
ggagtcccac tggggtatcc catcaaggcc cccaagctgc ctggtggcta tggactgccc     660
tacaccacag ggaaactgcc ctatggctat gggcccggag gagtggctgg tgcagcgggc     720
```

| | | |
|---|---|---|
| aaggctggtt acccaacagg gacaggggtt ggcccccagg cagcagcagc agcggcagct | 780 | |
| aaagcagcag caaagttcgg tgctggagca gccggagtcc tccctggtgt tggaggggct | 840 | |
| ggtgttcctg gcgtgcctgg ggcaattcct ggaattggag gcatcgcagg cgttgggact | 900 | |
| ccagctgcag ctgcagctgc agcagcagcc gctaaggcag ccaagtatgg agctgctgca | 960 | |
| ggcttagtgc ctggtgggcc aggctttggc ccgggagtag ttggtgtccc aggagctggc | 1020 | |
| gttccaggtg ttggtgtccc aggagctggg attccagttg tcccaggtgc tgggatccca | 1080 | |
| ggtgctgcgg ttccagggt tgtgtcacca gaagcagctg ctaaggcagc tgcaaaggca | 1140 | |
| gccaaatacg gggccaggcc cggagtcgga gttggaggca ttcctactta cggggttgga | 1200 | |
| gctgggggct ttcccggctt tggtgtcgga gtcggaggta tccctggagt cgcaggtgtc | 1260 | |
| cctagtgtcg gaggtgttcc cggagtcgga ggtgtcccgg agttggcat ttcccccgaa | 1320 | |
| gctcaggcag cagctgccgc caaggctgcc aagtacggtc tgcaggagc aggagtgctg | 1380 | |
| ggtgggctag tgccaggtcc ccaggcggca gtcccaggtg tgccgggcac gggaggagtg | 1440 | |
| ccaggagtgg ggaccccagc agctgcagct gctaaagcag ccgccaaagc cgcccagttt | 1500 | |
| gggttagttc ctggtgtcgg ggtggctcct ggagttggcg tggctcctgg tgtcggtgtg | 1560 | |
| gctcctggag ttggcttggc tcctggagtt ggcgtggctc ctggagttgg tgtggctcc | 1620 | |
| ggcgttggcg tggctcccgg cattggcccct ggtggagttg cagctgcagc aaaatccgct | 1680 | |
| gccaaggtgc ctgccaaagc ccagctccga gctgcagctg gcttggtgc tggcatccct | 1740 | |
| ggacttggag ttggtgtcgg cgtccctgga cttggagttg tgctggtgt tcctggactt | 1800 | |
| ggagttggtc ctggtgttcc tggcttcggg gcagtacctg gagccgatga gggagttagg | 1860 | |
| cggagcctgt cccctgagct cagggaagga gatccctcct cctctcagca cctccccagc | 1920 | |
| accccctcat cacccagggt acctggagcc ctggctgccg ctaaagcagc caaatatgga | 1980 | |
| gcagcagtgc ctggggtcct tggagggctc ggggctctcg gtggagtagg catcccaggc | 2040 | |
| ggtgtggtgg gagccggacc cgccgccgcc gctgccgcag ccaaagctgc tgccaaagcc | 2100 | |
| gcccagtttg gcctagtggg agccgctggg ctcggaggac tcggagtcgg agggcttgga | 2160 | |
| gttccaggtg ttggggcct tggaggtata cctccagctg cagccgctaa agcagctaaa | 2220 | |
| tacggtgctg ctggccttgg aggtgtccta gggggtgccg ggcagttccc acttggagga | 2280 | |
| gtggcagcaa gacctggctt cggattgtct cccattttcc caggtggggc ctgcctgggg | 2340 | |
| aaagcttgtg gccggaagag aaaatga | 2367 | |

<210> SEQ ID NO 6
<211> LENGTH: 417
<212> TYPE: PRT
<213> ORGANISM: Homo sapiens

<400> SEQUENCE: 6

Met Arg Phe Ala Trp Thr Val Leu Leu Leu Gly Pro Leu Gln Leu Cys
1               5                   10                  15

Ala Leu Val His Cys Ala Pro Pro Ala Gly Gln Gln Gln Pro Pro
            20                  25                  30

Arg Glu Pro Pro Ala Ala Pro Gly Ala Trp Arg Gln Gln Ile Gln Trp
        35                  40                  45

Glu Asn Asn Gly Gln Val Phe Ser Leu Leu Ser Leu Gly Ser Gln Tyr
    50                  55                  60

Gln Pro Gln Arg Arg Arg Asp Pro Gly Ala Ala Val Pro Gly Ala Ala
65                  70                  75                  80

-continued

```
Asn Ala Ser Ala Gln Gln Pro Arg Thr Pro Ile Leu Leu Ile Arg Asp
                85                  90                  95
Asn Arg Thr Ala Ala Arg Thr Arg Thr Ala Gly Ser Ser Gly Val
            100                 105                 110
Thr Ala Gly Arg Pro Arg Pro Thr Ala Arg His Trp Phe Gln Ala Gly
            115                 120                 125
Tyr Ser Thr Ser Arg Ala Arg Glu Arg Gly Ala Ser Arg Ala Glu Asn
        130                 135                 140
Gln Thr Ala Pro Gly Glu Val Pro Ala Leu Ser Asn Leu Arg Pro Pro
145                 150                 155                 160
Ser Arg Val Asp Gly Met Val Gly Asp Pro Tyr Asn Pro Tyr Lys
                165                 170                 175
Tyr Ser Asp Asp Asn Pro Tyr Tyr Asn Tyr Tyr Asp Thr Tyr Glu Arg
            180                 185                 190
Pro Arg Pro Gly Gly Arg Tyr Arg Pro Gly Tyr Gly Thr Gly Tyr Phe
        195                 200                 205
Gln Tyr Gly Leu Pro Asp Leu Val Ala Asp Pro Tyr Tyr Ile Gln Ala
    210                 215                 220
Ser Thr Tyr Val Gln Lys Met Ser Met Tyr Asn Leu Arg Cys Ala Ala
225                 230                 235                 240
Glu Glu Asn Cys Leu Ala Ser Thr Ala Tyr Arg Ala Asp Val Arg Asp
                245                 250                 255
Tyr Asp His Arg Val Leu Leu Arg Phe Pro Gln Arg Val Lys Asn Gln
            260                 265                 270
Gly Thr Ser Asp Phe Leu Pro Ser Arg Pro Arg Tyr Ser Trp Glu Trp
        275                 280                 285
His Ser Cys His Gln His Tyr His Ser Met Asp Glu Phe Ser His Tyr
    290                 295                 300
Asp Leu Leu Asp Ala Asn Thr Gln Arg Arg Val Ala Glu Gly His Lys
305                 310                 315                 320
Ala Ser Phe Cys Leu Glu Asp Thr Ser Cys Asp Tyr Gly Tyr His Arg
                325                 330                 335
Arg Phe Ala Cys Thr Ala His Thr Gln Gly Leu Ser Pro Gly Cys Tyr
            340                 345                 350
Asp Thr Tyr Gly Ala Asp Ile Asp Cys Gln Trp Ile Asp Ile Thr Asp
        355                 360                 365
Val Lys Pro Gly Asn Tyr Ile Leu Lys Val Ser Val Asn Pro Ser Tyr
    370                 375                 380
Leu Val Pro Glu Ser Asp Tyr Thr Asn Asn Val Val Arg Cys Asp Ile
385                 390                 395                 400
Arg Tyr Thr Gly His His Ala Tyr Ala Ser Gly Cys Thr Ile Ser Pro
                405                 410                 415
Tyr
```

<210> SEQ ID NO 7
<211> LENGTH: 1254
<212> TYPE: DNA
<213> ORGANISM: Homo sapiens

<400> SEQUENCE: 7

```
atgcgcttcg cctggaccgt gctcctgctc gggcctttgc agctctgcgc gctagtgcac    60
tgcgcccctc ccgccgccgg ccaacagcag ccccgcgcg agccgccggc ggctccgggc   120
gcctggcgcc agcagatcca atgggagaac aacgggcagg tgttcagctt gctgagcctg   180
```

```
ggctcacagt accagcctca gcgccgccgg gacccgggcg ccgccgtccc tggtgcagcc    240
aacgcctccg cccagcagcc ccgcactccg atcctgctga tccgcgacaa ccgcaccgcc    300
gcggcgcgaa cgcggacggc cggctcatct ggagtcaccg ctggccgccc caggcccacc    360
gcccgtcact ggttccaagc tggctactcg acatctagag cccgcgaacg tggcgcctcg    420
cgcgcggaga accagacagc gccgggagaa gttcctgcgc tcagtaacct gcggccgccc    480
agccgcgtgg acggcatggt gggcgacgac ccttacaacc cctacaagta ctctgacgac    540
aacccttatt acaactacta cgatacttat gaaaggccca gacctggggg caggtaccgg    600
cccggatacg gcactggcta cttccagtac ggtctcccag acctggtggc cgacccctac    660
tacatccagg cgtccacgta cgtgcagaag atgtccatgt acaacctgag atgcgcggcg    720
gaggaaaact gtctggccag tacagctac agggcagatg tcagagatta tgatcacagg     780
gtgctgctca gatttcccca aagagtgaaa aaccaaggga catcagattt cttacccagc    840
cgaccaagat attcctggga atggcacagt tgtcatcaac attaccacag tatggatgag    900
tttagccact atgacctgct tgatgccaac acccagagga gagtggctga aggccacaaa    960
gcaagtttct gtcttgaaga cacatcctgt gactatggct accacaggcg atttgcatgt   1020
actgcacaca cacagggatt gagtcctggc tgttatgata cctatggtgc agacatagac   1080
tgccagtgga ttgatattac agatgtaaaa cctggaaact atatcctaaa ggtcagtgta   1140
aaccccagct acctggttcc tgaatctgac tataccaaca atgttgtgcg ctgtgacatt   1200
cgctacacag gacatcatgc gtatgcctca ggctgcacaa tttcaccgta ttag         1254

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
gacataaccg acgtgcagcc                                                  20

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
atccacgttc gctccctgag                                                  20

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
gtatataccc aggtggcgtg                                                  20

<210> SEQ ID NO 11
<211> LENGTH: 21
<212> TYPE: DNA
<213> ORGANISM: Artificial sequence
<220> FEATURE:
<223> OTHER INFORMATION: Primer
```

<400> SEQUENCE: 11
cgaactttgc tgctgcttta g                                                    21

<210> SEQ ID NO 12
<211> LENGTH: 23
<212> TYPE: DNA
<213> ORGANISM: Artificial sequence
<220> FEATURE:
<223> OTHER INFORMATION: Primer

<400> SEQUENCE: 12
ggtggccgac ccctactaca tcc                                                  23

<210> SEQ ID NO 13
<211> LENGTH: 26
<212> TYPE: DNA
<213> ORGANISM: Artificial sequence
<220> FEATURE:
<223> OTHER INFORMATION: Primer

<400> SEQUENCE: 13
gcaaatcgcc tctggtagcc atagtc                                               26

<210> SEQ ID NO 14
<211> LENGTH: 18
<212> TYPE: DNA
<213> ORGANISM: Artificial sequence
<220> FEATURE:
<223> OTHER INFORMATION: Primer

<400> SEQUENCE: 14
gtggagagta ctggattg                                                        18

<210> SEQ ID NO 15
<211> LENGTH: 18
<212> TYPE: DNA
<213> ORGANISM: Artificial sequence
<220> FEATURE:
<223> OTHER INFORMATION: Primer

<400> SEQUENCE: 15
tcgtgcagcc atcgacag                                                        18

<210> SEQ ID NO 16
<211> LENGTH: 26
<212> TYPE: DNA
<213> ORGANISM: Artificial sequence
<220> FEATURE:
<223> OTHER INFORMATION: Primer

<400> SEQUENCE: 16
ttggatccag cgtaggcagc gtgtac                                               26

<210> SEQ ID NO 17
<211> LENGTH: 25
<212> TYPE: DNA
<213> ORGANISM: Artificial sequence
<220> FEATURE:
<223> OTHER INFORMATION: Primer

<400> SEQUENCE: 17
aaactcgagc atcgtagtcg gtggc                                                25

<210> SEQ ID NO 18

```
<211> LENGTH: 29
<212> TYPE: DNA
<213> ORGANISM: Artificial sequence
<220> FEATURE:
<223> OTHER INFORMATION: Primer

<400> SEQUENCE: 18
tcggatccgg ctactcgaca tctagagcc                                        29

<210> SEQ ID NO 19
<211> LENGTH: 27
<212> TYPE: DNA
<213> ORGANISM: Artificial sequence
<220> FEATURE:
<223> OTHER INFORMATION: Primer

<400> SEQUENCE: 19
gtcctcgaga ccgtactgga agtagcc                                          27

<210> SEQ ID NO 20
<211> LENGTH: 29
<212> TYPE: DNA
<213> ORGANISM: Artificial sequence
<220> FEATURE:
<223> OTHER INFORMATION: Primer

<400> SEQUENCE: 20
ttggatccgt gcagaagatg tccatgtac                                        29

<210> SEQ ID NO 21
<211> LENGTH: 29
<212> TYPE: DNA
<213> ORGANISM: Artificial sequence
<220> FEATURE:
<223> OTHER INFORMATION: Primer

<400> SEQUENCE: 21
tttctcgagg ctgggtaaga aatctgatg                                        29

<210> SEQ ID NO 22
<211> LENGTH: 28
<212> TYPE: DNA
<213> ORGANISM: Artificial sequence
<220> FEATURE:
<223> OTHER INFORMATION: Primer

<400> SEQUENCE: 22
cactatggat cccttgatgc caacaccc                                         28

<210> SEQ ID NO 23
<211> LENGTH: 27
<212> TYPE: DNA
<213> ORGANISM: Artificial sequence
<220> FEATURE:
<223> OTHER INFORMATION: Primer

<400> SEQUENCE: 23
cacgaccttt aggatatcgt ttccagg                                          27

<210> SEQ ID NO 24
<211> LENGTH: 20
<212> TYPE: DNA
<213> ORGANISM: Artificial sequence
<220> FEATURE:
<223> OTHER INFORMATION: Primer

<400> SEQUENCE: 24
```

```
gtatataccc aggtggcgtg                                                   20

<210> SEQ ID NO 25
<211> LENGTH: 21
<212> TYPE: DNA
<213> ORGANISM: Artificial sequence
<220> FEATURE:
<223> OTHER INFORMATION: Primer

<400> SEQUENCE: 25
cgaactttgc tgctgcttta g                                                 21

<210> SEQ ID NO 26
<211> LENGTH: 19
<212> TYPE: DNA
<213> ORGANISM: Artificial sequence
<220> FEATURE:
<223> OTHER INFORMATION: Primer

<400> SEQUENCE: 26
gacttcggca acctcaagc                                                    19

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
tgttgcagaa acgtagcgac                                                   20

<210> SEQ ID NO 28
<211> LENGTH: 21
<212> TYPE: DNA
<213> ORGANISM: Artificial sequence
<220> FEATURE:
<223> OTHER INFORMATION: Primer

<400> SEQUENCE: 28
acgtacgtgc agaagatgtc c                                                 21

<210> SEQ ID NO 29
<211> LENGTH: 21
<212> TYPE: DNA
<213> ORGANISM: Artificial sequence
<220> FEATURE:
<223> OTHER INFORMATION: Primer

<400> SEQUENCE: 29
ggctgggtaa gaaatctgat g                                                 21

<210> SEQ ID NO 30
<211> LENGTH: 20
<212> TYPE: DNA
<213> ORGANISM: Artificial sequence
<220> FEATURE:
<223> OTHER INFORMATION: Primer

<400> SEQUENCE: 30
gtggggcgcc ccaggcacca                                                   20

<210> SEQ ID NO 31
<211> LENGTH: 24
<212> TYPE: DNA
```

```
<213> ORGANISM: Artificial sequence
<220> FEATURE:
<223> OTHER INFORMATION: Primer

<400> SEQUENCE: 31
ctccttaatg tcacgcacga tttc                                            24
```